United States Patent
Ruzicka et al.

(10) Patent No.: US 12,338,197 B2
(45) Date of Patent: Jun. 24, 2025

(54) PROCESS FOR PREPARATION OF AMIDES AND ESTERS OF 2-((2-HYDROXYPROPANOYL)OXY)PROPANOIC ACID

(71) Applicant: Univerzita Pardubice, Polabiny (CZ)

(72) Inventors: Aleš Ruzicka, Choltice (CZ); Roman Olejník, Drenice (CZ)

(73) Assignee: Univerzita Pardubice, Polabiny (CZ)

( * ) Notice: Subject to any disclaimer, the term of this patent is extended or adjusted under 35 U.S.C. 154(b) by 618 days.

(21) Appl. No.: 17/416,489

(22) PCT Filed: Dec. 16, 2019

(86) PCT No.: PCT/CZ2019/000060
§ 371 (c)(1),
(2) Date: Jun. 20, 2021

(87) PCT Pub. No.: WO2020/125823
PCT Pub. Date: Jun. 25, 2020

(65) Prior Publication Data
US 2022/0041542 A1  Feb. 10, 2022

(30) Foreign Application Priority Data
Dec. 19, 2018  (CS) ................. CZ2018-716

(51) Int. Cl.
*C07C 231/02* (2006.01)
*B01J 27/08* (2006.01)
(Continued)

(52) U.S. Cl.
CPC ............ *C07C 231/02* (2013.01); *B01J 27/08* (2013.01); *B01J 27/10* (2013.01); *B01J 27/125* (2013.01);
(Continued)

(58) Field of Classification Search
None
See application file for complete search history.

(56) References Cited

U.S. PATENT DOCUMENTS

| 2,371,281 A | 3/1945 | Claborn |
| 2,827,378 A | 3/1958 | Glabe |

(Continued)

FOREIGN PATENT DOCUMENTS

| CZ | 2016133 A3 | 9/2017 |
| CZ | 306988 B6 | 11/2017 |

(Continued)

OTHER PUBLICATIONS

Hydrocarbons (IUPAC Gold Book, downloaded from https://goldbook.iupac.org/terms/view/H02889 on Jan. 12, 2024) (Year: 2024).*

(Continued)

*Primary Examiner* — Amy C Bonaparte
(74) *Attorney, Agent, or Firm* — Rivka Friedman

(57) ABSTRACT

The present invention describes method of preparation of amides of lactyl lactates of general formula I, where Z denotes to group of RR'—N and R represent alkyl, aryl or H from lactide and the lactide reacts with an aliphatic or aromatic amine with 1 to 100 carbon atoms of general formula RR'NH or with an aliphatic or aromatic ammonium hydrohalide with 1 to 100 carbon atoms of general formula RR'NH·HX, where X is selected from Cl, Br and I in a non-chlorinated organic aliphatic or aromatic solvent or in a melted mixture of lactide under solvent free condition, and when lactide reacts with amine, initiator derived from group of Lewis acids of halides of 4., 12., 13., and 14. group is added.

(Continued)

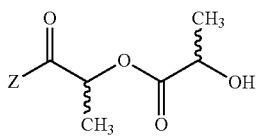

1 Claim, 3 Drawing Sheets

(51) Int. Cl.
B01J 27/10 (2006.01)
B01J 27/125 (2006.01)
B01J 27/135 (2006.01)
B01J 27/138 (2006.01)
C07C 67/03 (2006.01)

(52) U.S. Cl.
CPC ........... *B01J 27/135* (2013.01); *B01J 27/138* (2013.01); *C07C 67/03* (2013.01)

(56) References Cited

U.S. PATENT DOCUMENTS

| | | | |
|---|---|---|---|
| 5,688,850 A | 11/1997 | Wyffels | |
| 2011/0009661 A1* | 1/2011 | Tanaka | C07C 67/08 568/665 |
| 2011/0178339 A1* | 7/2011 | Van Krieken | C07C 231/02 564/134 |
| 2017/0298009 A1* | 10/2017 | Verkuijl | C07C 231/24 |

FOREIGN PATENT DOCUMENTS

| | | |
|---|---|---|
| WO | 2010037776 A1 | 4/2010 |
| WO | 2012066195 A1 | 5/2012 |

OTHER PUBLICATIONS

Toluene (PubChem CID 1140, downloaded from https://pubchem.ncbi.nlm.nih.gov/compound/Toluene#section=Boiling-Point&fullscreen=true on Jan. 12, 2024) (Year: 2024).*
Bigg ("Triethylamine/Aluminum Chloride Promoted Aminolysis of Lactones: A Useful Method for the Preparation of w-Hydroxyalkanamides" Synthesis, 1992, p. 277-278) (Year: 1992).*
Periodic Table (downloaded from https://www.acs.org/content/dam/acsorg/education/whatischemistry/periodic-table-of-elements/acs-periodic-table-poster_download.pdf on Sep. 19, 2024) (Year: 2024).*
Alba ("Direct ring-opening of lactide with amines: application to the organo-catalyzed preparation of amide end-capped PLA and to the removal of residual lactide from PLA samples" Polymer Chemistry, 2015, p. 989) (Year: 2015).*
Auras R. A.; L.-T. Lim; S.E.M Selke; H. Tsuji (2010), "Poly (lactic acid): Synthesis, Structures, Properties, Processing, and Applications", Wiley.com, only abstract and chapter titles provided.
Cherepakhin Valeriy S., Zaitsev Kirill V., "Catalytic synthesis of alkyl (S,S)—O-Lactyllactates: Efficiency in action", Catalysis Comm., 2018, 106, 36-39, only a printout of the abstract was provided.
Bigg Dennis C.H., Lesimple Patrick, "Triethylamine/aluminium chloride promoted aminolysis of lactones: A useful method for the preparation of ω-hydroxyalkanamides", Synthesis (Stuttgart), 1992, 3, 277-278.
R. Olejník, M. Bílek, Z. Růžičková et.al., "Zinc complexes chelated by bifunctional ketiminate ligands: Structure, reactivity and possible applications in initiation of ROP and copolymerization of epoxides with carbon dioxide", J. Organomet. Chem., 2015, 794, 237-246, only a printout of the abstract was provided.
P. Švec, P. Hubená, Z. Růžičková, et.al., "Poly(ethylene terephthalate) synthesis catalysed by chelated Sn, Zn and Mg complexes", Appl. Organometal. Chem., 2015, 30, 20-25, only a printout of the abstract was provided.
R. Olejník, J. Bažantová, Z. Růžičková, et.al., "Methoxyaryl substituted aluminum ketiminate complexes and its activity in ring opening polymerization processes", Inorg. Chem. Commun., 2015, 55, 161-164, only a printout of the abstract was provided.
H. Kampová, E. Riemlová, J. Klikarová, et.al., "Aluminium complexes containing N,N'-chelating amino-amide hybrid ligands applicable for preparation of biodegradable polymers", J. Organomet. Chem., 2014, 778, 35, only a printout of the abstract was provided.
R. Olejník, Z. Padělková, R. Mundil, et.al., "Tetrylenes chelated by bifunctional β-diketiminate ligand: Structure and possible applications", Appl. Organometal, Chem., 2014, 28, 405-412, only a printout of the abstract was provided.
T. Chlupatý, J. Merna, A. Růžička, "Bisguanidinato and bismidinato Tin(IV) diolates applicable in ring-opening polymerization", Catal. Commun., 2015, 60, 110-113.
F. Baiocchi, J.R. France, "Sodium isostearoyl-2-lactylate in cosmetics and toiletries", Cosmetics & Toiletries, 1978, 93, 47, only a printout of the abstract was provided.
K. Phomphrai, S. Pracha, P. Phonjanthuek, et.al., "Facile alcoholysis of l-lactide catalysed by Group 1 and 2 metal complexes", Dalton Trans., 2008, 3048.
A. Alba, O. Thillay du Boullay, M.-V. Blanca, et.al., "Direct ring-opening of lactide with amines: Application to the organocatalyzed preparation of amide end-capped PLA and to the removal of residual lactide from PLA samples", Polym. Chem., 2015, 6, 989-997.
M. Bednarek, M. Basko, T. Biedron, et.al., "Polymerization of lactide initiated by primary amines and catalyzed by a protic acid" Eur. Polym. J., 2015, 71, 380, a copy of the accepted unedited manuscript was provided.

* cited by examiner

A

B

PROCESS FOR PREPARATION OF AMIDES AND ESTERS OF 2-((2-HYDROXYPROPANOYL)OXY)PROPANOIC ACID

THE FIELD OF INVENTION (CLASSIFICATION)

The invention covered the field of organic chemistry and described the process of preparation of amides and esters of 2-((2-hydroxypropanoyl)oxy)propanoic acid.

STATE OF THE ART

In the last few decades, consumer awareness about composition of the materials that surround him and are in everyday contact is growing significantly. The awareness and pressure of customers onto manufacturers and their portfolio of environmentally friendly and biocompatible products is enormous, especially in the case of cosmetics and household products. Producers are striving to meet the market's needs, as is evident from the expanding range of environmentally friendly products, but on the other hand, their potential may be hampered by economic factors, the availability of environmentally friendly raw materials, or compatibility with the other components of the formulation. The solution could be synthesis of new biodegradable and biocompatible compounds such as polylactides or PLAs (formula A, FIG. 1) which are preferably derived from renewable resources and contain a theoretically unlimited number of molecules of lactic acid.

Polylactides are usually synthesized from lactides. The structure of lactide could be described as cyclic diester of 2-hydroxypropanoic acid (lactic acid) which formed six membered ring as a result of dehydration reaction in the presence of a catalyst.

The structure of lactide contains two chiral centers (depicted by asterisk in formula B, FIG. 2) because of different substitution on carbon atoms. This situation results to existence of various stereoisomers of lactide; as L-lactide [(S,S)-3,6-dimethyl-1,4-dioxane-2,5-dione], (formula C, FIG. 3), D-lactide [(R,R)-3,6-dimethyl-1,4-dioxane-2,5-dione], (formula D, FIG. 3), meso-lactide [(S,R)-3,6-dimethyl-1,4-dioxane-2,5-dione)], (formula E, FIG. 3). All these molecular structures could be described as formula F (FIG. 3).

This invention relates to all existing stereoisomers of lactide and mixtures thereof containing two or more stereoisomers of lactide in different molar ratios, for example a racemic lactide mixture composed of D-lactide and L-Lactide in the ratio 1:1.

Lactides play one of the main roles in the synthesis of polymers and copolymers [R. Auras; L.-T. Lim; S. E. M Selke; H. Tsuji (2010), Poly (lactic acid): Synthesis, Structures, Properties, Processing, and Applications, Wiley, ISBN 978-0-470-29366-9] with higher added value. These biocompatible and biodegradable oligomers/polymers currently appear to be an important substitution for fossil materials and can be produced in the long term from natural sources such as biomass, vegetable oil, corn, cotton, proteins for a wide range of cosmetics and household applications.

Polylactide polymers are usually synthesized from lactide monomers via ring-opening polymerization (ROP) in the presence of initiators based on complexes of (non-) transition metals M (M=Zn, lit.: R. Olejník, M. Bílek, Z. Růžičková, Z. Hoštálek, J. Merna, A. Růžička, J. Organomet. Chem., 2015, 794, 237; P. Švec, P. Hubená, Z. Růžičková, J. Holubová, M. Pouzar, J. Merna, A. Růžička, Appl. Organometal. Chem., 2015, 30, 20; Al, lit.: R. Olejnik, J. Bažantová, Z. Růžičková, J. Merna, Z. Hoštálek, A. Růžička, Inorg. Chem. Commun., 2015, 55, 161, H. Kampová, E. Riemlová, J. Klikarová, V. Pejchal, J. Merna, P. Vlasák, P. Švec, Z. Růžičková, A. Růžička, J. Organomet. Chem., 2014, 778, 35; Sn, lit.: R. Olejník, Z. Padělková, R. Mundil, J. Merna, A. Růžička, Appl. Organometal. Chem., 2014, 28, 405, T. Chlupatý, J. Merna, A. Růžička, Catal. Commun., 2015, 60, 110). The main disadvantage of this process is representing by possible leaking of metal-organic contaminants to oligo/polyester or polyamide product resulting in deterioration of toxicological profile.

Lactylates are structurally related to polylactides, and could be described as oligomeric structures depicted on Formula G (FIG. 4), where R denotes an alkyl or aryl substituent. Lactylates composed of two molecules of lactic acid and are usually produced from lactic acid and acyl chlorides of fatty acids (C8-C18) via esterification processes. Lactylates found application in the food industry as disclosed in U.S. Pat. No. 2,827,378A, especially in dough products. They improve crumb parameters such as texture, suppleness or durability, as well as they can be found in cosmetics and toiletries where act as biogenic surfactants with potential antiseptic effects, as described in F. Baiocchi, J. R. France, Cosmetics & Toiletries, 1978, 93, 47.

The structure of lactylates may be modified when different synthetic approach takes place. The procedure can combine ROP protocol, lactide monomer and oligomeric conditions. All these aspects result in developing lactyl lactates of the formulas H and J (FIG. 5), wherein R is alkyl, or aryl, and R is alkyl, aryl, or hydrogen.

The synthetic approach for the preparation of lactyl lactates is linked to two different functional groups (OH or COOH group) in the lactic acid. The carboxyl group may be activated and subsequently reacted with various substrates such as alcohols, amines, as well as with the hydroxyl group of lactic acid to form oligo-/polyesters/polyamides or mixtures thereof, and for this reason is also appropriate to reduce the potential side reactions and synthesized only one of the target oligomers or mixtures thereof with well-defined composition. This is usually done by protecting of reaction sides of lactic acid by convenient functional groups [K. Phomphrai, S. Pracha, P. Phonjanthuek, M. Pohmakotr, Dalton Trans., 2008, 3048.] but this synthetic way is connected to experimental difficulties.

For this reason, it is preferable to use a ROP strategy based on the lactide monomer for the synthesis of lactyl lactates. This approach is described in U.S. Pat. Nos. 2,371,281 and 5,688,850, wherein the products synthesized are hardly separable mixtures of individual oligomers/esters, and the whole synthesis is carried out under drastic conditions using concentrated sulfuric acid or benzene sulfonic acid as a catalyst. The lactyl lactates can be also synthesized via initiation with the volatile mineral acids described in CZ306988 as well as Lewis acids, for example $AlCl_3$ [V. S. Cherepakhin, K. V. Zaitsev, Catal. Commun, 2018, 106, 36].

Amides can be prepared from lactides and amines by ROP conditions, usually in several steps. The amine reacts autocatalytically with lactide and subsequently in the presence of 1,8-diazabicyclo[5.4.0]undec-7-ene (DBU) to polylactide as described in literature [A. Alba, O. Thillay du Boullay, M.-V. Blanca, D. Bourissou, Polym. Chem., 2015, 6, 98, or in WO2012006195]. Optionally, a protic acid such as HCl, $CH_3COOH$ etc. may be used in the second step instead of the base [M. Bednarek, M. Basko, T. Biedron, E. Wojtczak, A. Michalski, Eur. Polym. J., 2015, 71,380]. Some approaches works under solvent-free conditions, for example, the lactide can be dissolved at low temperature directly in the selected amine, for example dimethylamine. The ring-opening polymerization proceeds auto-catalytically with low temperature during initiation step, typically at temperatures −60° C., and the reaction produces a mixture of lactyl lactylated amide as well as lactic acid amide, as disclosed in WO 2010037776.

The object of the this invention is to provide a method for preparing amides and esters of 2-((2-hydroxypropanoyl)oxy)propanoic acid from lactide which is sufficiently selective, environmentally friendly and provides high yields.

DESCRIPTION

The present invention describes method of preparation of esters or amides of lactyl lactates of general formula I (FIG. 6), where Z denotes to group of R—O or RR'—N and R represent alkyl, aryl or H from lactide and the lactide is in contact with a hydrocarbyl alcohol and a hydrolyzable halide in a non-chlorinated organic solvent, or an amine initiated by a hydrolysable halide or hydrogen halide solution or an ammonium hydrohalide, wherein the hydrocarbyl alcohol or amine is either aliphatic or aromatic and containing 1 to 1000 carbon atoms, preferably 1 up to 150 carbon atoms, and optionally one or more, preferably 1 to 5, —$CH_2$— groups may be replaced by —O— groups.

In a preferred embodiment, the hydrocarbyl alcohol comprises of 1 to 100 hydroxyl groups, preferably 1 to 10 hydroxyl groups, and is selected from the group consisting of: methanol, 1-propanol, 1-butanol, 2-propanol, 2-methyl-2-propanol, 2-ethyl-1-hexanol, phenol, cyclohexanol, trimethylolpropane oxetane, trimethylolpropane diallyl ether, 1,4-butanediol, 1,5-pentanediol, 1,6-hexanediol, 1,10-decanediol, 1-octadecanol, oleyl alcohol, 1-hexadecanol, carbohydrates a polysaccharides, poly(vinyl-alcohols), polyethylene glycol, lignin, fatty alcohols etc.

In a preferred embodiment, the amine is selected from the group consisting of aliphatic primary and secondary amines, anilines and polyamines.

In a preferred embodiment, the reaction is carried out in aliphatic or aromatic organic solvent or in a melted mixture of lactide under solvent free conditions.

In a preferred embodiment, the reaction is carried out at temperature from 35 to 130° C. for 15 minutes to 8 hours.

In a preferred embodiment, the hydrolyzable halide is selected from the group of halides Al, B, Si, Ge, Sn, P, Ti, and Zr, wherein the halogen atom is selected from the group of Cl, Br and I.

In a preferred embodiment, the reaction mixture contains 0.001 to 0.05 molar equivalents of hydrolyzable halide or hydrogen halide relative to the lactide.

The following examples of embodiments do not limit the scope of protection given in the definition, but only illustrate the nature of the invention.

BRIEF DESCRIPTION OF THE DRAWINGS

The present invention will be explained in detail by means of the following figures where.

EXAMPLES OF EMBODIMENTS

The present invention is focused on the preparation of esters and amides from lactides and mono-/polyhydric alcohols or amines. The amines and alcohols may be aliphatic or aromatic, linear or branched, containing one or more functional amino or hydroxy groups in their structure. It is an object of the present invention to replace the hydrogen in these functional groups with a lactyl lactate molecule according to the reactions described in Schemes 1 and 2 in the presence of a Lewis acid as initiator of ring-opening polymerization (ROP) of lactide. The initiator is based on group 4, 12, 13 and 14 halides; or/and solution of hydrogen chloride in organic solvent; in the case of amide synthesis, the hydrochlorides of the corresponding amines can be used, in advance. A necessary condition is to prevent the access of water during the ROP reaction, and also to have the lactide and the alcohol or amine in the same phase.

Preparation of esters of
2-((2-hydroxypropanoyl)oxy)propanoic acid

Figure 1:
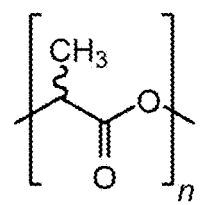
FIG. 1 shows formula A, where the main chain of polylactides or PLAs is shown.
Figure 2:
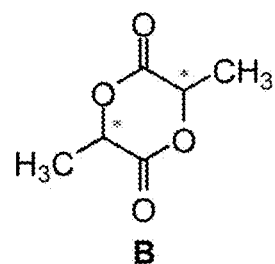
FIG. 2 shows formula B, where the structure of lactide containing two chiral centers is shown.
Figure 3:
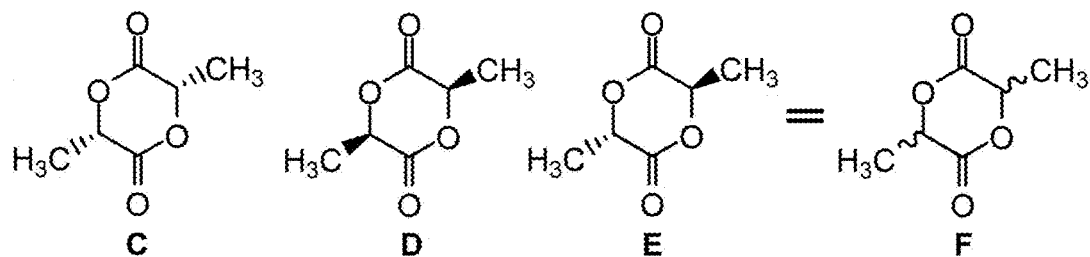
FIG. 3 shows various stereoisomers of lactide; as L-lactide [(S,S)-3,6-dimethyl-1,4-dioxane-2,5-dione] (formula C), D-lactide [(R,R)-3,6-dimethyl-1,4-dioxane-2,5-dione] (formula D), meso-lactide [(S,R)-3,6-dimethyl-1,4-dioxane-2,5-dione), (formula E), all these molecular structures could be described as formula F.
Figure 4:
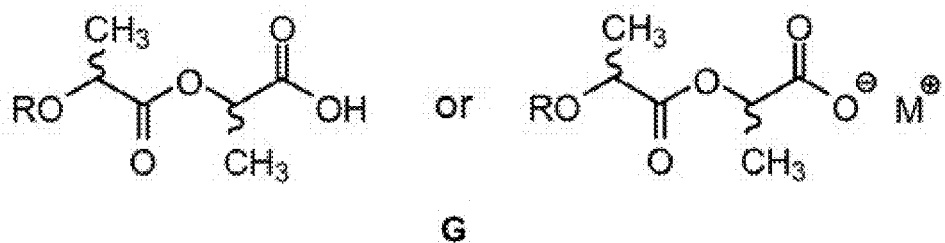
FIG. 4 shows lactylates that are structurally related to polylactides, and could be described as oligomeric structures depicted on formula G, where R denotes an alkyl or aryl substituent.
Figure 5:
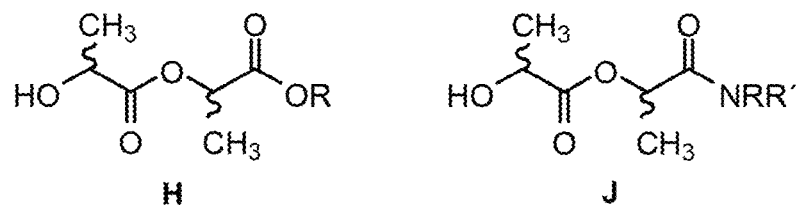
FIG. 5 shows lactyl lactates of the formulas H and J, wherein R is alkyl, or aryl, and R is alkyl, aryl, or hydrogen.
Figure 6:
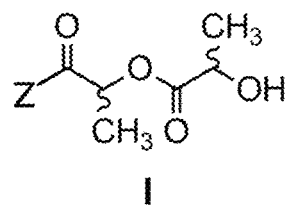
FIG. 6 shows esters or amides of lactyl lactates of general formula I according to the present invention.
Figure 7:
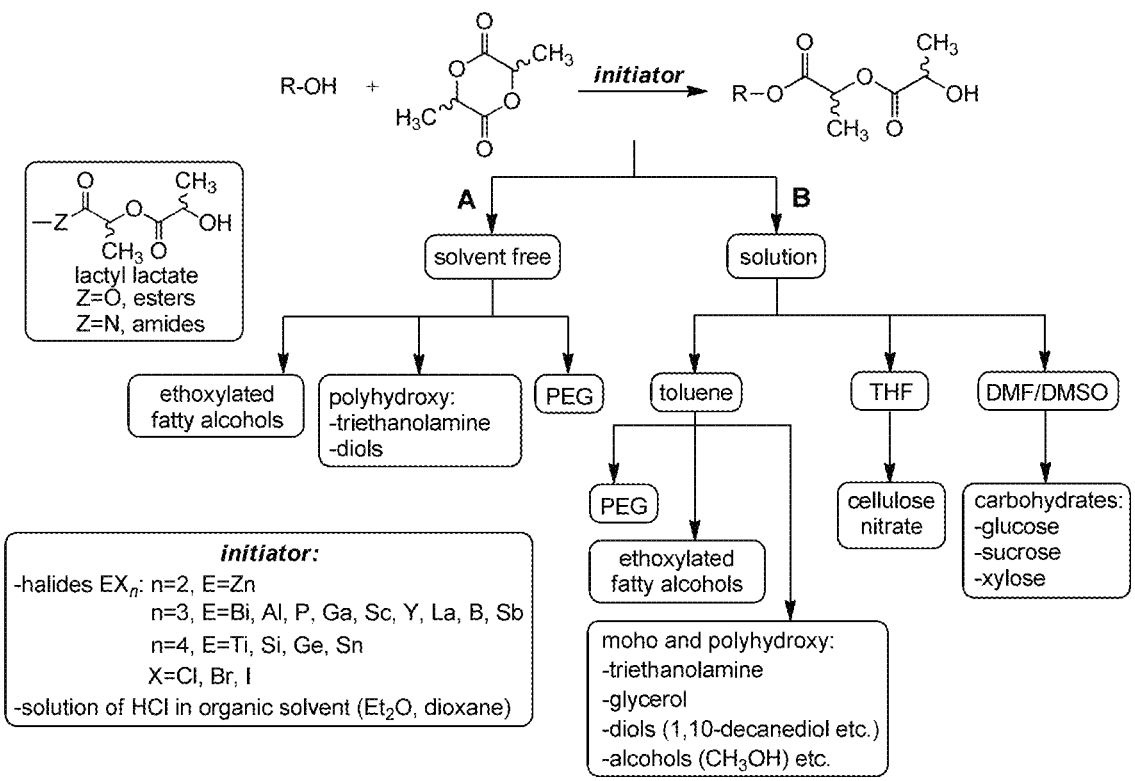
FIG. 7 shows preparation of esters on Scheme 1.

The present invention covers the reaction of lactide with substrate as is shown in the Scheme 1, FIG. 7.

The substrate is hydroxy derivative of general formula R—OH, where R is an alkyl or aryl substituent bearing one or more free hydroxy groups, for example alcohol, diol, polyalcohol, polyethylene glycol (PEG), carbohydrates etc. The proposed procedure describes substitution at least one or more hydrogen atoms of the original OH groups by lactyl lactate.

The reaction can be carried out as solvent free or in solution of organic solvent, as indicated in Scheme 1. A necessary condition of the invention is presence of lactide and ROH substrate in the same phase during at least a short period of time. It is usually achieved by excess of ROH substrate increasing the solubility of lactide at room temperature, for example mono- and polyhydric alcohols, or using the elevated temperatures. The reaction can be carried out in a solvent such as toluene for polyalcohols, tetrahydrofuran for cellulose nitrate or dimethylformamide (DMF) and dimethyl sulfoxide (DMSO), respectively, for polysaccharides such as glucose, sucrose and xylose. In the case of R—OH substrates melting at lower temperatures, such as PEG, ethoxylated fatty alcohols, or those where is lactide at least soluble or partially soluble at room or elevated temperature without using an excess of ROH, the reaction can be carried out in the melt as solvent free.

The reaction can be initiated by halides of general formula $EX_n$ of elements from groups 4, 12, 13 and 14, where X=Cl, Br or I and E=Zn, B, Al, P, Ga, Sc, Y, La, Bi, Sb, Ti, Si, Ge, Sn. In advance, a solution of HX in organic solvent, for example dioxane, $Et_2O$, may be used, or hydrogen halide gas may be collected directly in reaction mixture or selected alcohol which is one of the reactants. The reaction time depends on the type of ROH substrate and ranges from 2 to 8 hours; 2 hours usually for monohydric alcohols such as methanol, 8 hours for polysaccharides such as xylose. The reaction time also depends on the reaction pathway (Scheme 1) or whether is reaction proceed like solvent free or in solution of organic solvent. The physical parameters of oligomerization (homo vs. heterogeneous reaction) and the steric effects of the ROH substrate play an important role. The product separation depends on the selected synthetic pathway and is based on evaporation of the volatile components of the reaction mixture, such as hydrogen halides or organic solvents, filtration from the initiator residues, or precipitation of the product with an organic solvent such as methanol.

Preparation of amides of 2-((2-hydroxypropanoyl)oxy)propanoic acid

Figure 8:
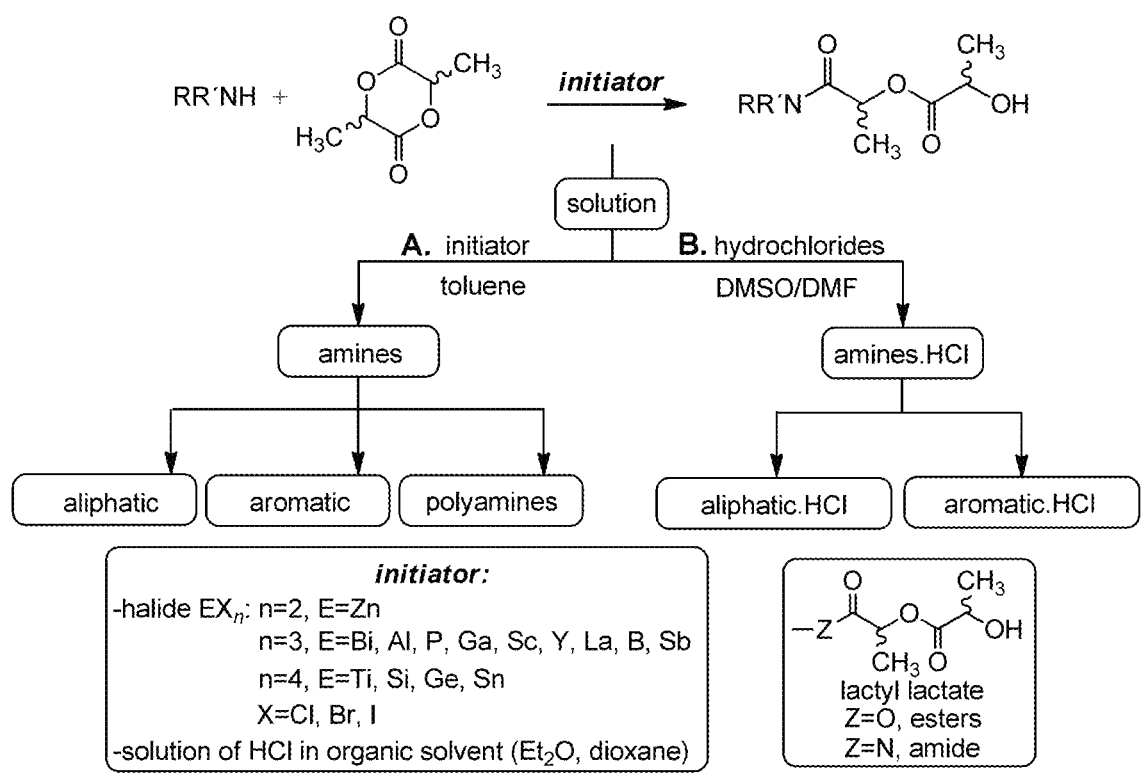
FIG. 8 shows preparation of amides on Scheme 2.

The present invention covers the reaction of lactide with substrate as is shown in the Scheme 2, FIG. 8.

The substrate is an amine RR'NH and R is alkyl or aryl substituent and R' is alkyl, an aryl substituent or hydrogen atom H, containing at least one or more amino groups, for example, an aliphatic or aromatic amine, linear or branched amine such as a polyethylenimine (PEI). The proposed procedure describes the substitution at least one or more of hydrogen atoms of original NH groups by molecules of lactyl lactate. The reaction can be initiated by halides of general formula $EX_n$ of elements from groups 4, 12, 13 and 14, where X=Cl, Br or I and E=Zn, B, Al, P, Ga, Sc, Y, La, Bi, Sb, Ti, Si, Ge, Sn, or by solution of HCl in $Et_2O$, dioxane or toluene as the preferred solvents. The method can be used for primary linear and branched amines, aliphatic amines such as 1-aminopropane or 2-aminopropane; aromatic amines similar to aniline and its derivatives, and poly(amines), for example PEI. The second process described in Scheme 2, reaction pathway B, is based on the reaction of a primary amine hydrochloride with lactide in the absence of initiator. The reaction proceeds in dimethyl sulfoxide (DMSO) or dimethylformamide (DMF) as priority solvents. In addition, amides containing structural fragments of lactyl lactate and amine derived from amine hydrochloride could by synthesized by this approach. The reaction time depends on the type of selected RR'NH substrate and ranges from 2 to 10 hours, 2 hours for monovalent linear amines such as 2-aminopropane, 10 hours for aromatic amines such as aniline, and also depends on the reaction pathway or whether is carried out in solution or directly with the quaternary ammonium salt, i.e. the hydrochloride, further to the degree of homogeneity of the reaction and the steric difficulty of the RR'NH substrate. The product separation depends on the selected preparation process and is based on evaporation of the volatile components of the reaction mixture, such as hydrogen halides or organic solvents, filtration from the initiator residues, or precipitation of the product with an organic solvent such as methanol.

Example 1: Reaction of Methanol with Lactide in Toluene Initiated by $AlCl_3$

A 25 ml round bottomed flask was loaded with 0.22 g of methanol (1 equiv., 0.28 ml, 6.938 mmol), 1.0 g of lactide (1 equiv., 6.938 mmol), 5 ml of toluene and heated to 80° C. with vigorous stirring. The lactide was dissolved after approx. 5 minutes and 50 mg of $AlCl_3$ (0.374 mmol) was added. Reaction mixture was stirred for 2 hours and filtered. All volatiles were evaporated under reduced pressure. The residue was dried to constant weight at 10° C./1 mbar.

The yield of product was 1.32 g (6.73 mmol, 97%). Anal. calcd for $C_7H_{12}O_5$ (%): C (47.72), H (6.87), O (45.41); found: C (47.7), H (6.6). $^1H$ NMR (500 MHz, $C_6D_6$, 298K): δ 5.02 (q, $J_{H-H}$=7.1 Hz, 1H, CH), 4.30 (q, $J_{H-H}$=7.1 Hz, 1H, CH), 3.80 (br s, 1H, HO), 3.29 (s, 3H, $CH_3$), 1.45 (d, $J_{H-H}$=7.0 Hz, 3H, $CH_3$) and 1.19 (d, $J_{H-H}$=7.2 Hz, 3H, $CH_3$). $^{13}C$ NMR (125 MHz, $C_6D_6$, 298K): δ 176.5 (C=O), 171.3 (C=O), 69.6 (CH), 67.3 (CH), 52.2 ($CH_3$), 20.8 ($CH_3$) and 17.0 ($CH_3$).

Example 2: Reaction of Methanol with Lactide in Excess of Methanol Initiated by Solution of HCl in $Et_2O$ A 25 ml round bottomed flask was loaded with 5.0 g of methanol (excess, 6.31 ml, 0.156 mol) and 1.0 g of lactide (1 equiv., 6.938 mmol). Reaction mixture was heated to 65° C. and stirred vigorously. The lactide was dissolved after approx. 5 minutes and 0.05 ml of solution of HCl in $Et_2O$ (1.0M, 0.05 mmol) was added. Reaction mixture was stirred for 2 hours/80° C. All volatiles were evaporated under reduced pressure. The residue was dried to constant weight at 40° C./1 mbar.

The yield of product was 1.22 g (6.86 mmol, 99%). Anal. calcd for $C_7H_{12}O_5$ (%): C (47.72), H (6.87), O (45.41); found: C (47.8), H (7.0). $^1H$ NMR (500 MHz, $C_6D_6$, 298K): δ 5.02 (q, $J_{H-H}$=7.1 Hz, 1H, CH), 4.30 (q, $J_{H-H}$=7.1 Hz, 1H, CH), 3.80 (br s, 1H, HO), 3.29 (s, 3H, $CH_3$), 1.45 (d, $J_{H-H}$=7.0 Hz, 3H, $CH_3$) and 1.19 (d, $J_{H-H}$=7.2 Hz, 3H, $CH_3$). $^{13}C$ NMR (125 MHz, $C_6D_6$, 298K): δ 176.5 (C=O), 171.3 (C=O), 69.6 (CH), 67.3 (CH), 52.2 ($CH_3$), 20.8 ($CH_3$) and 17.0 ($CH_3$).

Example 3: Reaction of Isopropyl Alcohol and Lactide in Excess of Isopropyl Alcohol Initiated by Solution of HCl in $Et_2O$ A 25 ml round bottomed flask was loaded with 7.0 g of $^iPrOH$ (excess, 8.90 ml, 0.116 mol), 1.0 g of lactide (1 equiv., 6.938 mmol) and heated to 80° C. with vigorous stirring. The lactide was dissolved after approx. 5 min and 0.05 ml of solution of HCl in $Et_2O$ (1.0M, 0.05 mmol) was added. Reaction mixture was stirred for 2 hours/80° C. All volatiles were evaporated under reduced pressure. The residue was dried to constant weight at 40° C./1 mbar.

The yield of product was 1.31 g (6.38 mmol, 92%). Anal. calcd for $C_9H_{16}O_5$ (%): C (52.93), H (7.90), O (39.17); found: C (52.9), H (8.0). $^1H$ NMR (500 MHz, $C_6D_6$, 298K): δ 4.99 (q, $J_{H-H}$=8.8 Hz, 1H, CH), 4.90 (m, 1H, CH), 4.31 (q, $J_{H-H}$=8.7 Hz, 1H, CH), 1.47 (d, $J_{H-H}$=8.7 Hz, 3H, $CH_3$) and 1.21 (d, $J_{H-H}$=8.9 Hz, 3H, $CH_3$), 0.98-0.96 (m, 6H, $(CH_3)_2$). $^{13}C$ NMR (125 MHz, $C_6D_6$, 298K): δ 175.6 (C=O), 170.4 (C=O), 70.0 (CH), 69.5 (CH), 67.4 (CH), 21.7 (($CH_3)_2$), 20.9 ($CH_3$) and 16.9 ($CH_3$).

Example 4: Solvent Free Reaction of Isopropyl Alcohol and Lactide Initiated by Solution of HCl in $Et_2O$ A 25 ml round bottomed flask was loaded with 0.42 g of $^iPrOH$ (1 equiv., 0.53 ml, 6.938 mol), 1.0 g of lactide (1 equiv., 6.938 mmol) and heated to 80° C. with vigorous stirring. The lactide was dissolved after approx. 15 min and 0.05 ml of solution of HCl in $Et_2O$ (1.0M, 0.05 mmol) was added. Reaction mixture was stirred for 2 hours/80° C. All volatiles were evaporated under reduced pressure. The residue was dried to constant weight at 40° C./1 mbar.

The yield of product was 1.28 g (6.24 mmol, 90%). Anal. calcd for $C_9H_{16}O_5$ (%): C (52.93), H (7.90), O (39.17); found: C (53.1), H (8.0). $^1$H NMR (500 MHz, $C_6D_6$, 298K): δ 4.99 (q, $J_{H-H}$=8.8 Hz, 1H, CH), 4.90 (m, 1H, CH), 4.31 (q, $J_{H-H}$=8.7 Hz, 1H, CH), 1.47 (d, $J_{H-H}$=8.7 Hz, 3H, $CH_3$), 1.21 (d, $J_{H-H}$=8.9 Hz, 3H, $CH_3$) and 0.98-0.96 (m, 6H, $(CH_3)_2$). $^{13}$C NMR (125 MHz, $C_6D_6$, 298K): δ 175.6 (C=O), 170.4 (C=O), 70.0 (CH), 69.5 (CH), 67.4 (CH). 21.7 (($CH_3)_2$). 20.9 ($CH_3$) and 16.9 ($CH_3$).

Example 5: Solvent Free Reaction of Isopropyl Alcohol with Lactide Initiated by SiCl$_4$ A 25 ml round bottomed flask was loaded with 0.42 g of $^i$PrOH (1 equiv., 0.53 ml, 6.938 mol), 1.0 g of lactide (1 equiv., 6.938 mmol) and heated to 80° C. with vigorous stirring. The lactide was dissolved after approx. 15 min and 0.05 ml of SiCl$_4$ (0.075 g, 0.442 mmol) was added. Reaction mixture was stirred for 2 hours/80° C. All volatiles were evaporated under reduced pressure. The residue was dried to constant weight at 40° C./1 mbar.

The yield of product was 1.25 g (6.10 mmol, 88%). Anal. calcd for $C_9H_{16}O_5$ (%): C (52.93), H (7.90), O (39.17); found: C (53.1), H (8.1). $^1$H NMR (500 MHz, $C_6D_6$, 298K): δ 4.99 (q, $J_{H-H}$=8.8 Hz, 1H, CH), 4.90 (m, 1H, CH), 4.31 (q, $J_{H-H}$=8.7 Hz, 1H, CH), 1.47 (d, $J_{H-H}$=8.7 Hz, 3H, $CH_3$), 1.21 (d, $J_{H-H}$=8.9 Hz, 3H, $CH_3$) and 0.98-0.96 (m, 6H, $(CH_3)_2$). $^{13}$C NMR (125 MHz, $C_6D_6$, 298K): δ 175.6 (C=O), 170.4 (C=O), 70.0 (CH), 69.5 (CH), 67.4 (CH), 21.7 (($CH_3)_2$), 20.9 ($CH_3$) and 16.9 ($CH_3$).

Example 6: Reaction of Isopropyl Alcohol with Lactide in Toluene Initiated by ZnCl$_2$ A 25 ml round bottomed flask was loaded with 0.42 g of $^i$PrOH (1 equiv., 0.53 ml, 6.938 mol), 1.0 g of lactide (1 equiv., 6.938 mmol), 5 ml of toluene and heated to 80° C. with vigorous stirring. The lactide was dissolved after approx. 5 min and 30 mg of ZnCl$_2$ (0.220 mmol) was added. Reaction mixture was stirred for 2 hours/80° C. and filtered. All volatiles were evaporated under reduced pressure. The residue was dried to constant weight at 40° C./1 mbar.

The yield of product was 1.29 g (6.30 mmol, 91%). Anal. calcd for $C_9H_{16}O_5$ (%): C (52.93), H (7.90), O (39.17); found: C (53.0), H (8.0). $^1$H NMR (500 MHz, $C_6D_6$, 298K): δ 4.99 (q, $J_{H-H}$=8.8 Hz, 1H, CH), 4.90 (m, 1H, CH), 4.31 (q, $J_{H-H}$=8.7 Hz, 1H, CH), 1.47 (d, $J_{H-H}$=8.7 Hz, 3H, $CH_3$), 1.21 (d, $J_{H-H}$=8.9 Hz, 3H, $CH_3$) and 0.98-0.96 (m, 6H, $(CH_3)_2$). $^{13}$C NMR (125 MHz, $C_6D_6$, 298K): δ 175.6 (C=O), 170.4 (C=O), 70.0 (CH), 69.5 (CH), 67.4 (CH), 21.7 (($CH_3)_2$), 20.9 ($CH_3$) and 16.9 ($CH_3$).

Example 7: Reaction of Cyclohexanol and Lactide in Toluene Initiated by LaBr$_3$ A 25 ml round bottomed flask was loaded with 0.69 g of cyclohexanol (1 equiv., 6.938 mmol), 1.0 g of lactide (1 equiv., 6.938 mmol), 5 ml of toluene and heated to 80° C. with vigorous stirring. The lactide was dissolved after approx. 5 minutes and 20 mg of LaBr$_3$ (0.052 mmol) was added. Reaction mixture was stirred for 4 hours/80° C. and filtered. All volatiles were evaporated under reduced pressure. The residue was dried to constant weight at 40° C./1 mbar.

The yield of product was 1.39 g (5.69 mmol, 82%). Anal. calcd for $C_{12}H_{20}O_5$ (%): C (59.00), H (8.15), O (32.75); found: C (59.4), H (8.4). $^1$H NMR (500 MHz, $C_6D_6$, 298K): δ 5.13 (q, $J_{H-H}$=7.1 Hz, 1H, CH), 4.72 (m, 1H, CH$^{CHex}$) 4.48 (q, $J_{H-H}$=8.3 Hz, 1H, CH), 3.58-3.53 (m, 4H, CH$^{CHex}$), 1.89-1.86 (m, 7H, $CH_3$)+$CH_2^{CHex}$) 1.49 (d, $J_{H-H}$=6.9 Hz, 3H, $CH_3$) and 1.31-1.25 (m, 2H, CH$^{CHex}$). $^{13}$C NMR (125 MHz, $C_6D_6$, 298K): δ 175.5 (C=O), 168.2 (C=O), 74.3 (CH), 69.6 (CH), 67.4, 31.9, 25.8 (C$^{CHex}$), 21.0 ($CH_3$), 17.2 ($CH_3$) and 15.9 (C$^{CHex}$).

Example 8: Reaction of Cyclohexanol and Lactide in Toluene Initiated by Solution of HCl in Dioxane A 25 ml round bottomed flask was loaded with 0.69 g of cyclohexanol (1 equiv., 6.938 mol), 1.0 g of lactide (1 equiv., 6.938 mmol), 5 ml of toluene and heated to 80° C. with vigorous stirring. The lactide was dissolved after approx. 5 minutes and 0.05 ml of solution of HCl in dioxane (4M solution, 0.20 mmol) was added. Reaction mixture was stirred for 3.5 hours/80° C. All volatiles were evaporated under reduced pressure The residue was dried to constant weight at 40° C./1 mbar.

The yield of product was 1.44 g (5.89 mmol, 85%). Anal. calcd for $C_{12}H_{20}O_5$ (%): C (59.00), H (8.15), O (32.75); found: C (58.7), H (7.9). $^1$H NMR (500 MHz, $C_6D_6$, 298K): δ 5.13 (q, $J_{H-H}$=7.1 Hz, 1H, CH), 4.72 (m, 1H, CH$^{CHex}$) 4.48 (q, $J_{H-H}$=8.3 Hz, 1H, CH), 3.58-3.53 (m, 4H, CH$^{CHex}$), 1.89-1.86 (m, 7H, $CH_3$)+$CH_2$CHex) 1.49 (d, $J_{H-H}$=6.9 Hz, 3H, $CH_3$) and 1.31-1.25 (m, 2H, CH$^{CHex}$)$^{13}$C NMR (125 MHz, $C_6D_6$, 298K): δ 175.5 (C=O), 168.2 (C=O), 74.3 (CH), 69.6 (CH), 67.4, 31.9, 25.8 (C$^{CHex}$), 21.0 ($CH_3$), 17.2 ($CH_3$) and 15.9 (C$^{CHex}$).

Example 9: Reaction of Phenol and Lactide in Toluene Initiated by YI$_3$

A 25 ml round bottomed flask was loaded with 0.65 g of phenol (1 equiv., 6.938 mol), 1.0 g of lactide (1 equiv., 6.938 mmol), 7 ml of toluene and heated to 80° C. with vigorous stirring. The lactide and phenol were dissolved after approx. 5 minutes and 0.025 g of YI$_3$ (0.053 mmol) was added. Reaction mixture was stirred for 6 hours/80° C. and filtered. All volatiles were evaporated under reduced pressure. The residue was dried to constant weight at 40° C./1 mbar.

The yield of product was 0.41 g (1.72 mmol, 25%). Anal. calcd for $C_{12}H_{14}O_5$ (%): C (60.50), H (5.92), O (33.58); found: C (60.9), (H 6.2). $^1$H NMR (500 MHz, $C_6D_6$, 298K): δ 7.00 (t, $J_{H-H}$=8.0 Hz, 2H, H$^{Ph}$), 6.80 (t, $J_{H-H}$=7.4 Hz, 1H, H$^{Ph}$), 6.41 (d, $J_{H-H}$=8.0 Hz, 2H, H$^{Ph}$), 4.94 (q, $J_{H-H}$=7.0 Hz, 1H, CH), 4.09 (q, $J_{H-H}$=7.0 Hz, 1H, CH), 1.33 (d, $J_{H-H}$=6.7 Hz, 3H, $CH_3$) and 1.24 (d, $J_{H-H}$=7.1 Hz, 3H, CH). $^{13}$C NMR (125 MHz, $C_6D_6$, 298K): δ 177.2 (C=O), 167.8 (C=O), 129.2, 124.1 and 113.2 (C$^P$h), 70.4 (CH), 67.7 (CH), 20.9 ($CH_3$) and 16.7 ($CH_3$).

Example 10: Reaction of Phenol and Lactide in Toluene Initiated by Solution of HCl in Dioxane A 25 ml round bottomed flask was loaded with 0.65 g of phenol (1 ekv., 6.938 mol), 1.0 g of lactide (1 ekv., 6.938 mmol), 7 ml of toluene and heated to 80° C. with vigorous stirring. The lactide and phenol were dissolved after approx. 5 minutes and 0.05 ml of solution of HCl in dioxane (4M solution, 0.20 mmol) was added. Reaction mixture was stirred for 6 hours/80° C. and filtered. All volatiles were evaporated under reduced pressure. The residue was dried to constant weight at 40° C./1 mbar.

The yield of product was 0.56 g (2.34 mmol, 34%). Anal. calcd for $C_{12}H_{14}O_5$ (%): C (60.50), H (5.92), O (33.58); found: C (60.7), (H 6.1). $^1$H NMR (500 MHz, $C_6D_6$, 298K): δ 7.00 (t, $J_{H-H}$=8.0 Hz, 2H, $H^{Ph}$), 6.80 (t, $J_{H-H}$=7.4 Hz, 1H, $H^{Ph}$), 6.41 (d, $J_{H-H}$=8.0 Hz, 2H, $H^{Ph}$), 4.94 (q, $J_{H-H}$=7.0 Hz, 1H, CH), 4.09 (q, $J_{H-H}$=7.0 Hz, 1H, CH), 1.33 (d, $J_{H-H}$=6.7 Hz, 3H, $CH_3$) and 1.24 (d, $J_{H-H}$=7.1 Hz, 3H, CH). $^{13}$C NMR (125 MHz, $C_6D_6$, 298K): δ 177.2 (C=O), 167.8 (C=O), 129.2, 124.1 and 113.2 ($C^{Ph}$), 70.4 (CH), 67.7 (CH), 20.9 ($CH_3$) and 16.7 ($CH_3$).

Example 11: Reaction of 1,4-Butanediol and Lactide in Toluene Initiated by Solution of HCl in $Et_2O$ A 25 ml round bottomed flask was loaded with 0.63 g of 1,4-butanediol (1 equiv., 0.61 ml, 6.938 mol), 1.0 g of lactide (1 ekv., 6.938 mmol), 5 ml of toluene and heated to 80° C. with vigorous stirring. The lactide was dissolved after approx. 5 minutes and 0.10 ml of solution of HCl in $Et_2O$ (1M solution, 0.1 mmol) was added. Reaction mixture was stirred for 3 hours/80° C. All volatiles were evaporated under reduced pressure. The residue was dried to constant weight at 40° C./1 mbar.

The yield of product was 1.35 g (5.76 mmol, 83%). Anal. calcd for $C_{10}H_{18}O_6$ (%): C (51.27), H (7.75), O (40.98); found: C (51.4), H (7.9). $^1$H NMR (500 MHz, $C_6D_6$, 298K): δ 5.06 (q, $J_{H-H}$=7.0 Hz, 1H, CH), 4.35 (q, $J_{H-H}$=7.5 Hz, 1H, CH), 4.21-4.14 (m, 2H, $CH_2^{Bu}$), 1.68-1.63 (m, H, $H^{Bu}$), 1.54-1.44 (m, 1H, $H^{Bu}$), 1.40 (d, $J_{H-H}$=7.0 Hz, 3H, ($CH_3$) and 1.36 (d, $J_{H-H}$=7.2 Hz, 3H, $CH_3$). $^{13}$C NMR (125 MHz, $C_6D_6$, 298K): δ 174.4 (C=O), 169.8 (C=O), 69.0 (CH), 66.7 (CH), 64.2 ($C^{Bu}$), 26.2 ($C^{Bu}$), 24.3 ($CH_3$), 19.1 ($CH_3$), 15.8 and 13.1 ($C^{Bu}$).

Example 12: Reaction of 1,4-Butanediol and Lactide in Toluene Initiated by $SnBr_4$ A 25 ml round bottomed flask was loaded with 0.63 g of 1,4-butanediol (1 equiv., 0.61 ml, 6.938 mol), 2.0 g of lactide (2 equiv., 13.876 mmol), 5 ml of toluene and heated to 80° C. with vigorous stirring. The lactide was dissolved after approx. 5 minutes and 50 mg of $SnBr_4$ (1.14 mmol) in 3 ml of toluene was added. Reaction mixture was stirred for 6 hours/80° C. and filtered. All volatiles were evaporated under reduced pressure. The residue was dried to constant weight at 40° C./1 mbar.

The yield of product was 1.34 g (3.54 mmol, 51%). Anal. calcd for $C_{16}H_{26}O_{10}$(%): C (50.79), H (6.93), O (42.28); found: C (50.6), H (7.0). $^1$H NMR (500 MHz, $C_6D_6$, 298K): δ 5.06 (q, $J_{H-H}$=7.0 Hz, 2H, CH), 4.35 (q, $J_{H-H}$=7.5 Hz, 2H, CH), 4.21-4.14 (m, 4H, $CH^{Bu}$), 1.68-1.63 (m, 2H, $H^{Bu}$), 1.54-1.44 (m, 2H, $H^{Bu}$), 1.36 (d, $J_{H-H}$=7.0 Hz, 6H, $CH_3$) and 1.40 (d, $J_{H-H}$=7.2 Hz, 6H, $CH_3$). $^{13}$C NMR (125 MHz, $C_6D_6$, 298K): δ 174.4 (C=O), 169.8 (C=O), 69.0 (CH), 66.7 (CH), 64.2 ($CH^{Bu}$), 61.1 ($CH^{Bu}$), 26.2 ($C^{Bu}$), 24.3 ($CH_3$), 19.1 ($CH_3$) and 15.8 ($C^{Bu}$).

Example 13: Solvent Free Reaction of 1,4-Butanediol and Lactide Initiated by $BI_3$ A 25 ml round bottomed flask was loaded with 0.63 g of 1,4-butanediol (1 equiv., 0.61 ml, 6.938 mol), 2.0 g of lactide (2 equiv., 13.876 mmol) and heated to 80° C. with vigorous stirring. The lactide was dissolved after approx. 20 minutes and 20 mg of $BI_3$ (0.051 mmol) was added. Reaction mixture was stirred for 6 hours/80° C. and filtered. All volatiles were evaporated under reduced pressure. The residue was dried to constant weight at 40° C./1 mbar.

The yield of product was 1.13 g (2.98 mmol, 43%). Anal. calcd for $C_{16}H_{26}O_{10}$(%): C (50.79), H (6.93), O (42.28); found: C (50.2), H (6.6). $^1$H NMR (500 MHz, $C_6D_6$, 298K): δ 5.06 (q, $J_{H-H}$=7.0 Hz, 2H, CH), 4.35 (q, $J_{H-H}$=7.5 Hz, 2H, CH), 4.21-4.14 (m, 4H, $CH^{Bu}$), 1.68-1.63 (m, 2H, $H^{Bu}$), 1.54-1.44 (m, 2H, $H^{Bu}$), 1.36 (d, $J_{H-H}$=7.0 Hz, 6H, $CH_3$) and 1.40 (d, $J_{H-H}$=7.2 Hz, 6H, $CH_3$). $^{13}$C NMR (125 MHz, $C_6D_6$, 298K): δ 174.4 (C=O), 169.8 (C=O), 69.0 (CH), 66.7 (CH), 64.2 ($CH^{Bu}$), 61.1 ($CH^{Bu}$), 26.2 ($C^{Bu}$), 24.3 ($CH_3$) and 19.1 ($CH_3$), 15.8 ($C^{Bu}$).

Example 14: Solvent Free Reaction of 1,10-Decanediol and Lactide Initiated by $TiCl_4$ A 25 ml round bottomed flask was loaded with 0.5 g of 1,10-decanediol (1 equiv., 2.869 mmol), 0.83 g of lactide (2 equiv., 5.738 mmol) and heated to 80° C. with vigorous stirring. The lactide and 1,10-decanediol were mixed after approx. 15 minutes and 0.02 ml of $TiCl_4$ (34.6 mg, 0.182 mmol) was added. Reaction mixture was stirred for 6 hours/80° C. and filtered. All volatiles were evaporated under reduced pressure. The residue was dried to constant weight at 40° C./1 mbar.

The yield of product was 0.89 g (1.92 mmol, 67%). Anal. calcd for $C_{22}H_{38}O_{10}$(%): C (57.13), H (8.28), O (34.59); found: C (57.2) H (8.4). $^1$H NMR (500 MHz, $C_6D_6$, 298K): δ 5.05 (q, $J_{H-H}$=7.0 Hz, 2H, CH), 4.25 (q, $J_{H-H}$=7.0 Hz, 2H, CH), 3.97-3.94 (m, 4H, $CH^{Dec}$), 1.48 (d, $J_{H-H}$=7.0 Hz, 6H, $CH_3$), 1.39-1.37 (m, 4H, $H^{Dec}$), 1.24-1.22 (m, 10H, $H^{Dec}$ and $CH_3$) and 1.12 (br s, 8H, $H^{Dec}$). $^{13}$C NMR (125 MHz, $C_6D_6$, 298K): δ 175.7 (C=O), 170.8 (C=O), 69.0 (CH), 66.8 (CH), 67.3 ($CH^{Dec}$), 65.9 ($CH^{Dec}$), 30.0, 29.7, 29.1 and 26.3 ($C^{Dec}$). 21.0 ($CH_3$) and 17.4 ($CH_3$).

Example 15: Reaction of 1,10-Decanediol and Lactide in Toluene Initiated by $AlCl_3$ A 25 ml round bottomed flask was loaded with 0.5 g of 1,10-decanediol (1 equiv., 2.869 mmol), 0.83 g of lactide (2 equiv., 5.738 mmol), 10 ml of toluene and heated to 80° C. with vigorous stirring. The lactide and 1,10-decanediol were mixed after approx. 15 minutes and 20 mg of $AlCl_3$ (0.150 mmol) was added. Reaction mixture was stirred for 6 hours/80° C. and filtered. All volatiles were evaporated under reduced pressure. The residue was dried to constant weight at 40° C./1 mbar.

The yield of product was 1.09 g (2.35 mmol, 82%). Anal. calcd for $C_{22}H_{38}O_{10}$(%): C (57.13), H (8.28), O (34.59); Found: C (56.8), H (7.9). $^1$H NMR (500 MHz, $C_6D_6$, 298K): δ 5.05 (q, $J_{H-H}$=7.0 Hz, 2H, CH), 4.25 (q, $J_{H-H}$=7.0 Hz, 2H, CH), 3.97-3.94 (m, 4H, $CH^{Dec}$), 1.48 (d, $J_{H-H}$=7.0 Hz, 6H, $CH_3$), 1.39-1.37 (m, 4H, $H^{Dec}$), 1.24-1.22 (m, 10H, $H^{Dec}$ and $CH_3$) and 1.12 (br s, 8H, $H^{Dec}$). $^{13}$C NMR (125 MHz, $C_6D_6$, 298K): δ 175.7 (C=O), 170.8 (C=O), 69.0 (CH), 66.8 (CH), 67.3 ($CH^{Dec}$), 65.9 ($CH^{Dec}$), 30.0, 29.7, 29.1 and 26.3 ($C^{Dec}$), 21.0 ($CH_3$) and 17.4 ($CH_3$).

Example 16: Solvent Free Reaction of Triethanolamine and Lactide Initiated by $SiCl_4$ A 25 ml round bottomed flask was loaded with 1.0 g of triethanolamine (1 equiv., 6.703 mmol), 2.9 g of lactide (3 equiv., 20.102 mmol) and heated to 80° C. with vigorous stirring. The lactide was dissolved after approx. 15 minutes and 0.10 ml of SiCl$_4$ (0.15 g, 0.883 mmol) was added. Reaction mixture was stirred for 2 hours/80° C. All volatiles were evaporated under reduced pressure. The residue was dried to constant weight at 40° C./1 mbar.

The yield of product was 1.13 g (6.36 mmol, 95%). Anal. calcd for C$_{24}$H$_{39}$NO$_{15}$(%): C (49.47), H (6.76), O (41.27); found: C (49.8), H (6.9). $^1$H NMR (500 MHz, DMSO-d$_6$, 298K): δ 5.46-5.44 (m, 3H, OH), 5.04-4.99 (q, J$_{H-H}$=8.9 Hz, 3H, CH), 4.21-4.18 (m, 3H, CH), 4.11-4.10 (m, 6H, CH$_2$), 2.79-2.78 (m, 6H, CH$_2$), 1.42-1.40 (d, J$_{H-H}$=11.9 Hz, 9H, CH$_3$) and 1.30-1.28 (d, J$_{H-H}$=8.6 Hz, 9H, CH$_3$). $^{13}$C NMR (125 MHz, DMSO-d$_6$, 298K): δ 174.1 (C=O), 170.2 (C=O), 68.3 (CH), 65.6 (CH), 63.2 (CH$_2$), 52.4 (CH$_2$), 20.3 (CH$_3$) and 16.6 (CH$_3$).

Example 17: Reaction of Triethanolamine and Lactide in Toluene Initiated by AlCl$_3$ A 25 ml round bottomed flask was loaded with 1.0 g of triethanolamine (1 equiv., 6.703 mmol), 2.9 g of lactide (3 equiv., 20.102 mmol), 8 ml of toluene and heated to 80° C. with vigorous stirring. The lactide was dissolved after approx. 5 minutes and 0.12 g of AlCl$_3$ (0.883 mmol) was added. Reaction mixture was stirred for 2 hours/80° C. and filtered. All volatiles were evaporated under reduced pressure. The residue was dried to constant weight at 40° C./1 mbar.

The yield of product was 3.75 g (6.45 mmol, 96%). Anal. calcd for C$_{24}$H$_{39}$NO$_{15}$(%): C (49.47), H (6.76), O (41.27); found: C (49.7), H (6.9). $^1$H NMR (500 MHz, DMSO-d$_6$, 298K): δ 5.46-5.44 (m, 3H, OH), 5.04-4.99 (q, J$_{H-H}$=8.9 Hz, 3H, CH), 4.21-4.18 (m, 3H, CH), 4.11-4.10 (m, 6H, CH$_2$), 2.79-2.78 (m, 6H, CH$_2$), 1.42-1.40 (d, J$_{H-H}$=11.9 Hz, 9H, CH$_3$) and 1.30-1.28 (d, J$_{H-H}$=8.6 Hz, 9H, CH$_3$). $^{13}$C NMR (125 MHz, DMSO-d$_6$, 298K): δ 174.1 (C=O), 170.2 (C=O), 68.3 (CH), 65.6 (CH), 63.2 (CH$_2$), 52.4 (CH$_2$), 20.3 (CH$_3$) and 16.6 (CH$_3$).

Example 18: Reaction of Triethanolamine and Lactide in Toluene Initiated by Solution of HCl in Et$_2$O A 25 ml round bottomed flask was loaded with 1.0 g of triethanolamine (1 equiv., 6.703 mmol), 2.9 g of lactide (3 equiv., 20.102 mmol) and 8 ml of toluene and heated to 80° C. with vigorous stirring. The lactide was dissolved after approx. 5 minutes and 0.05 ml of solution of HCl in Et$_2$O (1.0M, 0.05 mmol) was added. Reaction mixture was stirred for 2 hours/80° C. and filtered. All volatiles were evaporated under reduced pressure. The residue was dried to constant weight at 40° C./1 mbar.

The yield of product was 3.81 g (6.55 mmol, 98%). Anal. calcd for C$_{24}$H$_{39}$NO$_{15}$(%): C (49.47), H (6.76), O (41.27); found: C (49.7), H (6.8). $^1$H NMR (500 MHz, DMSO-d$_6$, 298K): δ 5.46-5.44 (m, 3H, OH), 5.04-4.99 (q, J$_{H-H}$=8.9 Hz, 3H, CH), 4.21-4.18 (m, 3H, CH), 4.11-4.10 (m, 6H, CH$_2$), 2.79-2.78 (m, 6H, CH$_2$), 1.42-1.40 (d, J$_{H-H}$=11.9 Hz, 9H, CH$_3$) and 1.30-1.28 (d, J$_{H-H}$=8.6 Hz, 9H, CH$_3$). $^{13}$C NMR (125 MHz, DMSO-d$_6$, 298K): δ 174.1 (C=O), 170.2 (C=O), 68.3 (CH), 65.6 (CH), 63.2 (CH$_2$), 52.4 (CH$_2$), 20.3 (CH$_3$) and 16.6 (CH$_3$).

Example 19: Solvent Free Reaction of Ethoxylated Fatty Alcohol and Lactide Initiated by Solution of HCl in Et$_2$O A 25 ml round bottomed flask was loaded with 1.0 g of ethoxylated alcohol (trade name Genapol T200, 1 equiv., 0.999 mmol), 0.14 g of lactide (1 equiv., 0.999 mmol) and heated to 85° C. and vigorously stirred until both compounds were mixed in clear viscous mixture. After this period, 0.05 ml of solution of HCl in Et$_2$O (1.0M, 0.05 mmol) was added. Reaction mixture was stirred for 2 hours/80° C. All volatiles were evaporated under reduced pressure. The residue was dried to constant weight at 40° C./1 mbar.

The yield of product was 1.08 g (0.94 mmol, 94%). $^1$H NMR (500 MHz, DMSO-d$_6$, 298K): δ 5.49 (d, J$_{H-H}$=6.0 Hz, 1H, OH), 5.04 (q, J$_{H-H}$=7.1 Hz, 1H, CH), 4.21-4.16 (m, 3H, CH+CH$^{ethox}$), 3.51 (br s, 156H, CH$^{ethox}$), 3.45 (m, 8H, CH$^{ethox}$), 1.47-1.45 (m, 2H, H$^{ethox}$), 1.42-1.40 (d, J$_{H-H}$=6.5 Hz, 3H, CH$_3$), 1.30-1.24 (m, 64H, CH$_3$+H$^{ethox}$), 1.22 (br s, 30H, H$^{ethox}$) and 0.85 (t, J$_{H-H}$=6.7 Hz, 3H, CH$^{ethox}$) $^{13}$C NMR (125 MHz, DMSO-d$_6$, 298K): δ 174.2 (C=O), 168.6 (C=O), 72.4 and 70.4 (C$^{ethox}$), 69.8 (CH), 69.6 (C$^{ethox}$) 65.6 (CH), 64.1 and 60.2 (C$^{ethox}$), 31.4, 29.3, 29.1, 28.8 and 22.2 (C$^{ethox}$), 20.4 (CH$_3$), 15.1 (CH$_3$) and 13.9 (C$^{ethox}$).

Example 20: Reaction of Ethoxylated Fatty Alcohol and Lactide in Toluene Initiated by BiCl$_3$ A 25 ml round bottomed flask was loaded with 1.0 g of ethoxylated alcohol (trade name Genapol T200, 1 equiv., 0.999 mmol), 0.14 g of lactide (1 equiv., 0.999 mmol), 15 ml of toluene and heated to 85° C. with vigorous stirring. After 15 minutes 30 mg of BiCl$_3$ (0.063 mmol) in 5 ml of toluene was added. Reaction mixture was stirred for 6 hours/85° C. and filtered. All volatiles were evaporated under reduced pressure. The residue was dried to constant weight at 40° C./1 mbar.

The yield of product was 0.63 g (0.55 mmol, 55%). $^1$H NMR (500 MHz, DMSO-d$_6$, 298K): δ 5.49 (d, J$_{H-H}$=6.0 Hz, 1H, OH), 5.04 (q, J$_{H-H}$=7.1 Hz, 1H, CH), 4.21-4.16 (m, 3H, CH+CH$^{ethox}$), 3.51 (br s, 156H, CH$^{ethox}$), 3.45 (m, 8H, CH$^{ethox}$), 1.47-1.45 (m, 2H, H$^{ethox}$), 1.42-1.40 (d, J$_{H-H}$=6.5 Hz, 3H, CH$_3$), 1.30-1.24 (m, 64H, CH$_3$+H$^{ethox}$), 1.22 (br s, 30H, H$^{ethox}$) and 0.85 (t, J$_{H-H}$=6.7 Hz, 3H, CH$^{ethox}$)$^{13}$C NMR (125 MHz, DMSO-d$_6$, 298K): δ 174.2 (C=O), 168.6 (C=O), 72.4 and 70.4 (C$^{ethox}$), 69.8 (CH), 69.6 (C$^{ethox}$) 65.6 (CH), 64.1 and 60.2 (C$^{ethox}$), 31.4, 29.3, 29.1, 28.8 and 22.2 (C$^{ethox}$), 20.4 (CH$_3$), 15.1 (CH$_3$) and 13.9 (C$^{ethox}$).

Example 21: Reaction of PEG (M$_r$≈400 g/Mol) and Lactide in Toluene Initiated by GeBr$_4$ A 50 ml round bottomed flask was loaded with 1.0 g of polyethylene glycol (PEG, M$_r$≈400 g/mol, 1 equiv., 2.5 mmol), 0.36 g of lactide (1 equiv., 2.5 mmol), 10 ml of toluene and heated to 80° C. with vigorous stirring (5 minutes) until lactide was dissolved. After this period, 30 mg of GeBr$_4$ (0.076 mmol) in 5 ml of toluene was added. Reaction mixture was stirred for 6 hours/80° C. and filtered. All volatiles were evaporated under reduced pressure. The residue was dried to constant weight at 40° C./1 mbar.

The yield of product was 0.67 g (1.23 mmol, 49%). $^1$H NMR (500 MHz, C$_6$D$_6$, 298K): δ 5.42 (q, J$_{H-H}$=8.0 Hz, 2H, CH), 4.73 (q, J$_{H-H}$=7.0 Hz, 2H, CH), 3.50 (br s, 16H, H$^{PEG}$) 3.40 (t, J$_{H-H}$=5.2, 2H, H$^{PEG}$), 1.45 (d, J$_{H-H}$=7.0 Hz, 6H, CH$_3$) and 1.21 (d, J$_{H-H}$=7.2 Hz, 6H, CH$_3$). $^{13}$C NMR (125 MHz, C$_6$D$_6$, 298K): δ 175.2 (C=O), 170.2 (C=O), 72.4 (C$^{PEG}$) 71.1 (CH), 69.8 (C$^{PEG}$), 68.3 (CH), 60.1 (C$^{PEG}$), 20.8 (CH$_3$) and 17.0 (CH$_3$).

Example 22: Reaction of PEG (M$_r$≈400 g/Mol) and Lactide in Toluene Initiated by AlCl$_3$ A 50 ml round bottomed flask was loaded with 1.0 g of polyethylene glycol (PEG, M≈400 g/mol, 1 equiv., 2.5 mmol), 0.72 g of lactide (2 equiv., 5.0 mmol), 15 ml of toluene and heated to 80° C. with vigorous stirring. The lactide was dissolved after approx. 10 minutes and 20 mg of AlCl$_3$ (0.149 mmol) was added. Reaction mixture was stirred for 4 hours/80° C. and filtered. All volatiles were evaporated under reduced pressure. The residue was dried to constant weight at 40° C./1 mbar.

The yield of product was 1.07 g (1.55 mmol, 62%). $^1$H NMR (500 MHz, C$_6$D$_6$, 298K): δ 5.42 (q, J$_{H-H}$=8.0 Hz, 2H, CH), 4.73 (q, J$_{H-H}$=7.0 Hz, 2H, CH), 3.50 (br s, 16H, H$^{PEG}$) 3.40 (t, J$_{H-H}$=5.2, 2H, H$^{PEG}$), 1.45 (d, J$_{H-H}$=7.0 Hz, 6H, CH$_3$) and 1.21 (d, J$_{H-H}$=7.2 Hz, 6H, CH$_3$). $^{13}$C NMR (125 MHz, C$_6$D$_6$, 298K): δ 175.2 (C=O), 170.2 (C=O), 72.4 (C$^{PEG}$) 71.1 (CH), 69.8 (C$^{PEG}$), 68.3 (CH), 60.1 (C$^{PEG}$), 20.8 (CH$_3$) and 17.0 (CH$_3$).

Example 23: Solvent Free Reaction of PEG (M$_r$≈400 g/Mol) and Lactide Initiated by PCl$_3$ A 25 ml round bottomed flask was loaded with 1.0 g of polyethylene glycol (PEG, M≈400 g/mol, 1 equiv., 2.5 mmol), 0.72 g of lactide (2 equiv., 5.0 mmol) and heated to 80° C. with vigorous stirring. The lactide was dissolved after approx. 5 minutes and 30 mg of PCl$_3$ (19 μl, 0.218 mmol) was added. Reaction mixture was stirred for 4 hours/80° C. and filtered. All volatiles were evaporated under reduced pressure. The residue was dried to constant weight at 40° C./1 mbar.

The yield of product was 0.83 g (1.21 mmol, 48%). $^1$H NMR (500 MHz, C$_6$D$_6$, 298K): δ 5.42 (q, J$_{H-H}$=8.0 Hz, 2H, CH), 4.73 (q, J$_{H-H}$=7.0 Hz, 2H, CH), 3.50 (br s, 16H, H$^{PEG}$) 3.40 (t, J$_{H-H}$=5.2, 2H, H$^{PEG}$), 1.45 (d, J$_{H-H}$=7.0 Hz, 6H, CH$_3$) and 1.21 (d, J$_{H-H}$=7.2 Hz, 6H, CH$_3$). $^{13}$C NMR (125 MHz, C$_6$D$_6$, 298K): δ 175.2 (C=O), 170.2 (C=O), 72.4 (C$^{PEG}$) 71.1 (CH), 69.8 (C$^{PEG}$), 68.3 (CH), 60.1 (C$^{PEG}$), 20.8 (CH$_3$) and 17.0 (CH$_3$).

Example 24: Solvent Free Reaction of PEG (M$_r$≈1450 g/Mol) and Lactide Initiated by Solution of HCl in Dioxane A 25 ml round bottomed flask was loaded with 1.0 g polyethylene glycol (PEG, M$_r$≈1450 g/mol, 1 equiv., 0.690 mmol), 0.198 g of lactide (2 equiv., 1.38 mmol) and heated to 80° C. for approx. 20 minutes. The lactide was dissolved after this period and 0.05 ml of solution of HCl in dioxane (4M solution, 0.2 mmol) was added. Reaction mixture was stirred for 4 hours/80° C. All volatiles were evaporated under reduced pressure. The residue was dried to constant weight at 40° C./1 mbar.

The yield of product was 0.96 g (0.55 mmol, 80%). $^1$H NMR (500 MHz, C$_6$D$_6$, 298K): δ 5.42 (q, J$_{H-H}$=8.0 Hz, 2H, CH), 4.73 (q, J$_{H-H}$=7.0 Hz, 2H, CH), 3.50 (br s, 204H, H$^{PEG}$) 3.41-3.36 (m, 44H, H$^{PEG}$), 1.45 (d, J$_{H-H}$=7.0 Hz, 6H, CH$_3$) and 1.21 (d, J$_{H-H}$=7.2 Hz, 6H, CH$_3$). $^{13}$C NMR (125 MHz, C$_6$D$_6$, 298K): δ 175.4 (C=O), 169.8 (C=O), 72.4 (C$^{PEG}$), 71.0 (CH), 69.8 (C$^{PEG}$), 68.2 (CH), 60.2 (C$^{PEG}$), 20.8 (CH$_3$) and 17.0 (CH$_3$).

Example 25: Solvent Free Reaction of PEG (Mr≈1450 g/Mol) and Lactide Initiated by SbCl$_3$ A 25 ml round bottomed flask was loaded with 1.0 g of polyethylene glycol (PEG, M≈1450 g/mol, 1 equiv., 0.690 mmol), 0.198 g of lactide (2 equiv., 1.38 mmol) and heated to 80° C. with vigorous stirring. The lactide was dissolved after approx. 20 minutes and 15 mg of SbCl$_3$ (0.088 mmol) was added. Reaction mixture was stirred for 5 hours/80° C. and filtered. All volatiles were evaporated under reduced pressure. The residue was dried to constant weight at 40° C./1 mbar.

The yield of product was 0.53 g (0.30 mmol, 43%). $^1$H NMR (500 MHz, C$_6$D$_6$, 298K): δ 5.42 (q, J$_{H-H}$=8.0 Hz, 2H, CH), 4.73 (q, J$_{H-H}$=7.0 Hz, 2H, CH), 3.50 (br s, 204H, H$^{PEG}$) 3.41-3.36 (m, 44H, H$^{PEG}$), 1.45 (d, J$_{H-H}$=7.0 Hz, 6H, CH$_3$) and 1.21 (d, J$_{H-H}$=7.2 Hz, 6H, CH$_3$). $^{13}$C NMR (125 MHz, C$_6$D$_6$, 298K): δ 175.4 (C=O), 169.8 (C=O), 72.4 (C$^{PEG}$), 710 (CH), 69.8 (C$^{PEG}$), 68.2 (CH), 60.2 (C$^{PEG}$), 20.8 (CH$_3$) and 17.0 (CH$_3$).

Example 26: Reaction of Xylose and Lactide in DMF Initiated by Solution of HCl in Et$_2$O A 25 ml round bottomed flask was loaded with 1.0 g of xylose (1 equiv., 6.66 mmol), 0.96 g of lactide (1 equiv., 6.66 mmol), 10 ml of dimethylformamide (DMF) and heated to 80° C. with vigorous stirring. After this period, 0.1 ml of solution of HCl in Et$_2$O (1M solution, 0.1 mmol) was added. Reaction mixture was stirred for 6 hours/80° C. All volatiles were evaporated under reduced pressure. The residue was dried to constant weight at 40° C./1 mbar.

The yield of product was 1.33 g (4.52 mmol, 68%). $^1$H NMR (500 MHz, DMSO-d$_6$, 298K): δ 6.14 (d, J$_{H-H}$=5.8 Hz, 1H, CH$^{Xyl}$), 4.85-4.83 (m, 2H, CH$^{Xyl}$), 4.71-4.69 (m, 2H, CH$^{Xyl}$+CH), 4.48 (d, J$_{H-H}$=8.4 Hz, 1H, CH$^{Xyl}$), 4.24 (t, J$_{H-H}$=8.4, 1H, CH), 3.47-3.32 (m, 2H, CH$^{Xyl}$), 3.24-3.21 (m, 1H, CH$^{Xyl}$), 3.13-3.08 (m, 1H, CH$^{Xyl}$), 1.42 (d, J$_{H-H}$=8.0 Hz, 3H, CH$_3$) and 1.23 (d, J$_{H-H}$=7.6 Hz, 3H, CH$_3$). $^{13}$C NMR (125 MHz, DMSO-d$_6$, 298K): δ 170.7 (C=O), 160.8 (C=O), 92.6 (C$^{Xyl}$), 73.4, 72.5, 70.4 (C$^{Xyl}$), 70.2 (CH), 64.6 (CH), 61.6 (C$^{Xyl}$), 19.1 (CH$_3$) and 13.9 (CH$_3$).

Example 27: Reaction of Xylose and Lactide in DMSO Initiated by AlCl$_3$

A 25 ml round bottomed flask was loaded with 1.0 g of xylose (1 equiv., 6.66 mmol), 0.96 g of lactide (1 equiv., 6.66 mmol), 10 ml of dimethyl sulfoxide (DMSO) and heated to 80° C. with vigorous stirring. After this period, 30 mg of AlCl$_3$ (0.23 mmol) was added. Reaction mixture was stirred for 6 hours/80° C. and filtered. All volatiles were evaporated under reduced pressure. The residue was dried to constant weight at 70° C./1 mbar.

The yield of product was 1.33 g (4.52 mmol, 68%). $^1$H NMR (500 MHz, DMSO-d$_6$, 298K): δ 6.14 (d, J$_{H-H}$=5.8 Hz, 1H, CH$^{Xyl}$), 4.85-4.83 (m, 2H, CH$^{Xyl}$), 4.71-4.69 (m, 2H, CH$^{Xyl}$+CH), 4.48 (d, J$_{H-H}$=8.4 Hz, 1H, CH$^{Xyl}$), 4.24 (t, J$_{H-H}$=8.4, 1H, CH), 3.47-3.32 (m, 2H, CH$^{Xyl}$), 3.24-3.21 (m, 1H, CH$^{Xyl}$), 3.13-3.08 (m, 1H, CH$^{Xyl}$), 1.42 (d, J$_{H-H}$=8.0 Hz, 3H, CH$_3$) and 1.23 (d, J$_{H-H}$=7.6 Hz, 3H, CH$_3$). $^{13}$C NMR (125 MHz, DMSO-d$_6$, 298K): δ 170.7 (C=O), 160.8 (C=O), 92.6 (C$^{Xyl}$), 73.4, 72.5, 70.4 (C$^{Xyl}$), 70.2 (CH), 64.6 (CH), 61.6 (C$^{Xyl}$), 19.1 (CH$_3$) and 13.9 (CH$_3$).

Example 28: Reaction of Cellulose Nitrate and Lactide in THF Initiated by Solution of HCl in Et$_2$O A 50 ml round bottomed flask was loaded with 1.0 g of cellulose nitrate prepared from its 4-8% solution in Et$_2$O/ ethanol via solvent evaporation; 1.0 g of lactide (6.938 mmol) and 20 ml of tetrahydrofuran (THF). Reaction mixture was heated to 70° C. with vigorous stirring. After this period, 0.3 ml of solution of HCl in Et$_2$O (1M solution, 0.3 mmol) was added. Reaction mixture was stirred for 5 hours/70° C. All volatiles were evaporated under reduced pressure. The residue was dried to constant weight at 40° C./1 mbar The yield of product was 1.52 g. $^1$H NMR (500 MHz, DMSO-d$_6$, 298K): δ 5.03-4.91 (m, CH), 4.21-4.05 (m, CH), 3.79-3.63 (m, H$^{nitro}$), 1.74 (m, H$^{nitro}$), 1.29 (m, CH$_3$+H$^{nitro}$) and 1.23-1.16 (m, CH$_3$+H$^{nitro}$).

Example 29: Reaction of Poly(Vinyl-Alcohol) (PVA) and Lactide in DMSO Initiated by Solution of HCl in Et$_2$O A 100 ml round bottomed flask was loaded with 5.0 g of poly(vinyl-alcohol) (PVA, M≈9000 g/mol, 0.56 mmol), 2.5 g of lactide (17.35 mmol), 50 ml of dimethyl sulfoxide (DMSO) and heated to 80° C. with vigorous stirring. The poly(vinyl-alcohol) was dissolved after approx. 2 hours and 0.5 ml of solution of HCl in Et$_2$O (1M solution, 0.5 mmol) was added. Reaction mixture was stirred for 6 hours/80° C. and filtered. All volatiles were evaporated under reduced pressure; distillation residue was washed with 50 ml of hot toluene and filtered. The filtration residue was dried to constant weight at 70° C./1 mbar.

$^1$H NMR (500 MHz, DMSO-d$_6$, 298K): δ 4.95-4.87 (m, 1H, CH), 4.21-4.16 (m, 1H, CH), 4.00-3.82 (m, CH$^{PVA}$), 1.93 (s, CH$_3$$^{PVA}$), 1.34-1.31 (m, 3H, CH$_3$) and 1.20-1.18 (d, 3H, CH$_3$).

Example 30: Reaction of 1-Aminopropane and Lactide in Toluene Initiated by Solution of HCl in Et$_2$O A 25 ml round bottomed flask was loaded with 0.5 ml of 1-aminopropane (0.36 g, 1 equiv., 6.082 mmol), 0.88 g of lactide (1 equiv., 6.82 mmol), 8 ml of toluene and heated to 80° C. with vigorous stirring. The lactide was dissolved after approx. 10 minutes and 0.05 ml of solution of HCl in Et$_2$O (1M solution, 0.05 mmol) was added. Reaction mixture was stirred for 5 hours/80° C. and filtered. All volatiles were evaporated under reduced pressure. The residue was dried to constant weight at 40° C./1 mbar.

The yield of product was 0.31 g (1.52 mmol, 25%). Anal. calcd for C$_9$H$_{17}$NO$_4$ (%): C (53.19), H (8.43), N (6.89), O (31.49); found: C (53.4), H (8.5). $^1$H NMR (500 MHz, DMSO-d$_6$, 298K): δ 4.95-4.91 (m, 1H, CH), 4.21-4.16 (m, 1H, CH), 3.93 (m, 1H, OH), 3.05-3.00 (m, 2H, H$^{Pr}$), 2.29 (s, 1H, NH), 1.39-1.31 (m, 5H, CH$_3$+H$^{Pr}$), 1.20 (d, $J_{H-H}$=9.0 Hz, 3H, CH$_3$) and 0.83-0.80 (t, $J_{H-H}$=9.0 Hz, 3H, H$^{Pr}$). $^{13}$C NMR (125 MHz, DMSO-d$_6$, 298K): δ 173.9 (C=O), 169.7 (C=O), 70.7 (CH), 67.3 (CH), 65.5 (C$^{Pr}$), 22.5 (C$^{Pr}$), 21.2 (CH$_3$), 17.7 (CH$_3$) and 11.2 (C$^{Pr}$).

Example 31: Reaction of 1-Aminopropane and Lactide in Toluene Initiated by GaI$_3$ A 25 ml round bottomed flask was loaded with 0.5 ml of 1-aminopropane (0.36 g, 1 equiv., 6.082 mmol), 0.88 g of lactide (1 equiv., 6.082 mmol), 8 ml of toluene and heated to 80° C. with vigorous stirring. The lactide was dissolved after approx. 10 minutes and 15 mg of GaI$_3$ (0.03 mmol) was added. Reaction mixture was stirred for 5 hours/80° C. and filtered. All volatiles were evaporated under reduced pressure. The residue was dried to constant weight at 40° C./1 mbar.

The yield of product was 0.27 g (1.33 mmol, 22%). Anal. calcd for C$_9$H$_{17}$NO$_4$ (%): C (53.19), H (8.43), N (6.89), O (31.49); found: C (53.0), H (8.2). $^1$H NMR (500 MHz, DMSO-d$_6$, 298K): δ 4.95-4.91 (m, 1H, CH), 4.21-4.16 (m, 1H, CH), 3.93 (m, 1H, OH), 3.05-3.00 (m, 2H, H$^{Pr}$), 2.29 (s, 1H, NH), 1.39-1.31 (m, 5H, CH$_3$+H$^{Pr}$), 1.20 (d, $J_{H-H}$=9.0 Hz, 3H, CH$_3$) and 0.83-0.80 (t, $J_{H-H}$=9.0 Hz, 3H, H$^{Pr}$). $^{13}$C NMR (125 MHz, DMSO-d$_6$, 298K): δ 173.9 (C=O), 169.7 (C=O), 70.7 (CH), 67.3 (CH), 65.5 (C$^{Pr}$), 22.5 (C$^{Pr}$), 21.2 (CH$_3$), 17.7 (CH$_3$) and 11.2 (C$^{Pr}$).

Example 32: Reaction of Aniline and Lactide in Toluene Initiated by AlCl$_3$ A 25 ml round bottomed flask was loaded with 0.5 ml of aniline (phenylamine, 0.49 g, 1 equiv. 5.25 mmol), 0.76 g of lactide (1 equiv., 5.25 mmol), 8 ml of toluene and heated to 80° C. with vigorous stirring. The lactide and aniline were dissolved after approx. 10 minutes and 20 mg of AlCl$_3$ (0.15 mmol) was added. Reaction mixture was stirred for 5 hours/80° C. and filtered. All volatiles were evaporated under reduced pressure. The residue was dried to constant weight at 40° C./1 mbar.

The yield of product was 0.81 g (3.41 mmol, 65%). Anal. calcd for C$_{12}$H$_{15}$NO$_4$ (%): C (60.75), H (6.37), N (5.90), O (26.97); found: C (60.4), H (6.2). $^1$H NMR (500 MHz, DMSO-d$_6$, 298K): δ 7.62 (d, $J_{H-H}$=9.8 Hz, 1H, NH), 7.32 (t, $J_{H-H}$=9.4 Hz, 2H, H$^{Ar}$), 7.24-7.15 (m, 2H, H$^{Ar}$), 7.24-7.15 (m, 2H, H$^{Ar}$), 6.94-6.88 (m, 2H, H$^{Ar}$), 5.10 (q, $J_{H-H}$=8.7 Hz, 1H, CH), 4.24 (q, $J_{H-H}$=8.5 Hz, 1H, CH), 1.45 (d, $J_{H-H}$=8.3 Hz, 6H, CH$_3$) and 1.32 (d, $J_{H-H}$=8.6 Hz, 6H, CH$_3$). $^{13}$C NMR (125 MHz, DMSO-d$_6$, 298K): δ 175.3 (C=O), 170.2 (C=O), 132.5, 128.8, 118.8 and 115.0 (CH$^{Ar}$), 69.1 (CH), 65.9 (CH), 21.2 (CH$_3$) and 16.9 (CH$_3$).

Example 33: Reaction of Aniline Hydrochloride and Lactide in DMSO

A 25 ml round bottomed flask was loaded with 0.5 g of aniline hydrochloride (1 equiv., 3.86 mmol), 0.56 g of lactide (1 equiv., 3.86 mmol), 10 ml of dimethyl sulfoxide (DMSO) and heated to 80° C. Reaction mixture was stirred for 7 hours/80° C. and filtered. All volatiles were evaporated under reduced pressure. The residue was dried to constant weight at 40° C./1 mbar.

The yield of product was 0.48 g (2.02 mmol, 52%). Anal. calcd for C$_{12}$H$_{15}$NO$_4$ (%): C (60.75), H (6.37), N (5.90), O (26.97); found: C (60.9), H (6.6). $^1$H NMR (500 MHz, DMSO-d$_6$, 298K): δ 7.62 (d, $J_{H-H}$=9.8 Hz, 1H, NH). 7.32 (t, $J_{H-H}$=9.4 Hz, 2H, H$^{Ar}$), 7.24-7.15 (m, 2H, H$^{Ar}$), 7.24-7.15 (m, 2H, H$^{Ar}$), 6.94-6.88 (m, 2H, H$^{Ar}$), 5.10 (q, $J_{H-H}$=8.7 Hz, 1H, CH), 4.24 (q, $J_{H-H}$=8.5 Hz, 1H, CH), 1.45 (d, $J_{H-H}$=8.3 Hz, 6H, CH$_3$) and 1.32 (d, $J_{H-H}$=8.6 Hz, 6H, CH$_3$). $^{13}$C NMR (125 MHz, DMSO-d$_6$, 298K): δ 175.3 (C=O), 170.2 (C=O), 132.5, 128.8, 118.8 and 115.0 (CH$^{Ar}$), 69.1 (CH), 65.9 (CH), 21.2 (CH$_3$) and 16.9 (CH$_3$).

Example 34: Reaction of Diethylamine and Lactide in Toluene Initiated by Solution of HCl in Et$_2$O A 25 ml round bottomed flask was loaded with 0.5 ml of diethylamine (0.35 g, 1 equiv. 4.83 mmol), 0.69 g of lactide (1 equiv., 4.83 mmol), 10 ml of toluene and heated to 80° C. with vigorous stirring. The lactide was dissolved after approx. 5 minutes and 0.02 ml of solution of HCl in Et$_2$O (2M solution, 0.04 mmol) was added. Reaction mixture was stirred for 8 hours/80° C. and filtered. All volatiles were evaporated under reduced pressure. The residue was dried to constant weight at 40° C./1 mbar.

The yield of product was 0.28 g (1.29 mmol, 27%). Anal. calcd for $C_{10}H_{19}NO_4$ (%): C (55.28), H (8.81), N (6.45), O (29.46); found: C (55.0), H (8.6). $^1$H NMR (500 MHz, DMSO-$d_6$, 298K): δ 4.64 (t, $J_{H-H}$=8.2 Hz, 1H, CH), 4.21 (t, $J_{H-H}$=8.0, 1H, CH), 3.02-2.96 (m, 4H, $CH^{Et}$), 1.42 (d, $J_{H-H}$=8.0 Hz, 3H, $CH_3$), 1.23 (d, $J_{H-H}$=7.6 Hz, 3H, $CH_3$), 1.23 (d, $J_{H-H}$=7.6 Hz, 3H, $CH_3$) and 1.12 (t, $J_{H-H}$=7.2 Hz, 6H, $CH^{Et}$). $^{13}$C NMR (125 MHz, DMSO-$d_6$, 298K): δ 172.3 (C=O), 164.2 (C=O), 70.2 (CH), 64.6 (CH), 45.3 ($C^{Et}$), 17.0 ($CH_3$), 15.6 ($C^{Et}$) and 13.2 ($CH_3$).

Example 35: Reaction of Diethylamine and Lactide in Toluene Initiated by $SnBr_4$ A 25 ml round bottomed flask was loaded with 0.5 ml of diethylamine (0.35 g, 1 equiv. 4.83 mmol), 0.69 g of lactide (1 equiv., 4.83 mmol), 10 ml of toluene and heated to 80° C. with vigorous stirring. The lactide was dissolved after approx. 5 minutes and 30 mg of $SnBr_4$ (0.068 mmol) was added. Reaction mixture was stirred for 8 hours/80° C. and filtered. All volatiles were evaporated under reduced pressure. The residue was dried to constant weight at 40° C./1 mbar.

The yield of product was 0.24 g (1.105 mmol, 23%). Anal. calcd for $C_{10}H_{19}NO_4$ (%): C (55.28), H (8.81), N (6.45), O (29.46); found: C (55.3), H (9.0). $^1$H NMR (500 MHz, DMSO-$d_6$, 298K): δ 4.64 (t, $J_{H-H}$=8.2 Hz, 1H, CH), 4.21 (t, $J_{H-H}$=8.0, 1H, CH), 3.02-2.96 (m, 4H, $CH^{Et}$), 1.42 (d, $J_{H-H}$=8.0 Hz, 3H, $CH_3$), 1.23 (d, $J_{H-H}$=7.6 Hz, 3H, $CH_3$), 1.23 (d, $J_{H-H}$=7.6 Hz, 3H, $CH_3$) and 1.12 (t, $J_{H-H}$=7.2 Hz, 6H, $CH^{Et}$). $^{13}$C NMR (125 MHz, DMSO-$d_6$, 298K): δ 172.3 (C=O), 164.2 (C=O), 70.2 (CH), 64.6 (CH), 45.3 ($C^{Et}$), 17.0 ($CH_3$), 15.6 ($C^{Et}$) and 13.2 ($CH_3$).

Example 36: Reaction of Polyethylenimine and Lactide in Toluene Initiated by $AlCl_3$ A 25 ml round bottomed flask was loaded with 1.0 g of polyethylenimine (PEI, M≈600 g/mol, 1 equiv. 1.67 mmol), 1.44 g of lactide (6 equiv., 0.010 mol), 15 ml of toluene and heated to 80° C. with vigorous stirring. The lactide was dissolved after approx. 5 minutes and 10 mg of $AlCl_3$ (0.075 mmol) in 5 ml of toluene was added. Reaction mixture was stirred for 5 hours/80° C. and filtered. All volatiles were evaporated under reduced pressure. The residue was dried to constant weight at 40° C./1 mbar.

The yield of product was 1.06 g (0.76 mmol, 45%). $^1$H NMR (500 MHz, DMSO-$d_6$, 298K): δ 8.01-7.83 (m, $H^{PEI}$), 5.15 (m, 6H, CH), 4.39 (m, 6H, CH), 2.81-2.61 (m, $H^{PEI}$) and 1.43-1.39 (m, 36H, $CH_3$). $^{13}$C NMR (125 MHz, DMSO-$d_6$, 298K): δ 175.2 (C=O), 168.9 (C=O), 67.8 (CH), 62.9 (CH), 58.2, 54.5, 52.7, 49.3, 47.4, 41.6 ($C^{PEI}$), 21.3 ($CH_3$) and 14.3 ($CH_3$).

Example 37: Reaction of Polyethylenimine and Lactide in Toluene Initiated by Solution of HCl in $Et_2O$ A 50 ml round bottomed flask was loaded with 1.0 g of polyethylenimine (PEI, M≈600 g/mol, 1 equiv., 1.67 mmol), 1.44 g of lactide (6 equiv., 0.010 mol), 5 ml of toluene and heated to 80° C. with vigorous stirring. The lactide was dissolved after 5 minutes and 0.01 ml of solution of HCl in $Et_2O$ (2M solution, 0.02 mmol) was added. Reaction mixture was stirred for 5 hours/80° C. and filtered. All volatiles were evaporated under reduced pressure. The residue was dried to constant weight at 40° C./1 mbar.

The yield of product was 0.56 g (0.40 mmol, 24%). $^1$H NMR (500 MHz, DMSO-$d_6$, 298K): δ 8.01-7.83 (m, $H^{PEI}$), 5.15 (m, 6H, CH), 4.39 (m, 6H, CH), 2.81-2.61 (m, $H^{PEI}$) and 1.43-1.39 (m, 36H, $CH_3$). $^{13}$C NMR (125 MHz, DMSO-$d_6$, 298K): δ 175.2 (C=O), 168.9 (C=O), 67.8 (CH), 62.9 (CH), 58.2, 54.5, 52.7, 49.3, 47.4, 41.6 ($C^{PEI}$), 21.3 ($CH_3$) and 14.3 ($CH_3$).

Example 38: Reaction of 5-Amino-1-Pentanol and Lactide in Toluene Initiated by Solution of $BCl_3$ in Toluene A 25 ml round bottomed flask was loaded with 0.50 g of 5-amino-1-pentanol (0.525 ml, 1 equiv., 4.847 mmol), 1.40 g of lactide (AP, 2 equiv., 9.694 mmol), 10 ml of toluene and heated to 80° C. with vigorous stirring. The lactide was dissolved after approx. 5 minutes and 0.02 ml of $BCl_3$ in toluene (1M solution, 0.02 mmol) was added. Reaction mixture was stirred for 8 hours/80° C. and filtered. All volatiles were evaporated under reduced pressure. The residue was dried to constant weight at 40° C./1 mbar.

The yield of product was 0.043 g (0.11 mmol, 24%). Anal. calcd for $C_{17}H_{29}NO_9$ (%): C (52.17), H (7.47), N (3.58), O (36.79); found: C (52.5), H (7.7). $^1$H NMR (500 MHz, DMSO-$d_6$, 298K): δ 4.93-4.87 (m, 2H, CH), 4.33-4.30 (m, 2H, CH), 3.63 (t, $J_{H-H}$=7.8 Hz, 2H, $CH^{AP}$), 3.01 (t, $J_{H-H}$=8.6 Hz, 2H, $CH^{AP}$), 2.72 (br s, 1H, NH), 1.92-1.89 (m, 6H, $CH^{AP}$), 1.44 (d, $J_{H-H}$=8.6 Hz, 6H, $CH_3$) and 1.26 (d, $J_{H-H}$=8.6 Hz, 6H, $CH_3$). $^{13}$C NMR (125 MHz, DMSO-$d_6$, 298K): δ 171.8 (C=O), 168.8 (C=O), 71.3 (CH), 66.3 (CH), 60.5 ($C^{AP}$), 40.8, 33.2, 32.8, 22.0 ($C^{AP}$), 19.3 ($CH_3$) and 15.1 ($CH_3$).

Example 39: Reaction of 5-Amino-1-Pentanol and Lactide in Toluene Initiated by $GeCl_4$ A 25 ml round bottomed flask was loaded with 0.5 g of 5-amino-1-pentanol (AP, 0.525 ml, 1 equiv., 4.845 mmol), 0.70 g of lactide (1 equiv., 4.845 mmol), 10 ml of toluene and heated to 80° C. with vigorous stirring. The lactide was dissolved after approx. 5 minutes and 10 mg of $GeCl_4$ (0.047 mmol) in 2 ml of toluene was added. Reaction mixture was stirred for 8 hours/80° C. and filtered. All volatiles were evaporated under reduced pressure. The residue was dried to constant weight at 40° C./1 mbar.

The yield of product was 0.043 g (0.11 mmol, 24%). Anal. calcd for $C_{11}H_{21}NO_5$ (%): C (53.43), H (8.56), N (5.66), O (32.35); found: C (53.5), H (8.8). $^1$H NMR (500 MHz, DMSO-$d_6$, 298K): δ 4.88 (t, $J_{H-H}$=7.6 Hz, 1H, CH), 4.29 (t, $J_{H-H}$=8.0, 1 H, CH), 3.62 (t, $J_{H-H}$=7.6 Hz, 2H, $CH^{AP}$), 3.00 (t, $J_{H-H}$=8.6 Hz, 2H, $CH^{AP}$), 2.26 (br s, 2H, NH), 1.90-1.76 (m, 6H, $CH^{AP}$), 1.41 (d, $J_{H-H}$=8.0 Hz, 3H, $CH_3$) and 1.23 (d, $J_{H-H}$=8.0 Hz, 3H, $CH_3$). $^{13}$C NMR (125 MHz, DMSO-$d_6$, 298K): δ 172.3 (C=O), 167.8 (C=O), 70.6 (CH), 65.2 (CH), 60.6 ($C^{AP}$), 40.3, 33.3, 32.7, 22.1 ($C^{AP}$), 17.1 ($CH_3$) and 13.5 ($CH_3$).

Example 40: Reaction of 5-Amino-1-Pentanol Hydrochloride with Lactide in DMF

A 25 ml round bottomed flask was loaded with 0.70 g of 5-amino-1-pentanol hydrochloride (1 equiv., 5.03 mmol), 0.725 g of lactide (1 equiv., 5.03 mmol), 10 ml of dimethylformamide (DMF) and heated to 80° C. Reaction mixture was stirred for 8 hours/80° C. and filtered. All volatiles were evaporated under reduced pressure. The residue was dried to constant weight at 40° C./1 mbar.

The yield of product was 0.38 g (1.54 mmol, 31%). Anal. calcd for $C_{11}H_{21}NO_5$ (%): C (53.43), H (8.56), N (5.66), O (32.35); found: C (53.5), H (8.6). $^1$H NMR (500 MHz, DMSO-$d_6$, 298K): δ 4.88 (t, $J_{H-H}$=7.6 Hz, 1H, CH), 4.29 (t, $J_{H-H}$=8.0, 1 H, CH), 3.62 (t, $J_{H-H}$=7.6 Hz, 2H, $CH^{AP}$), 3.00 (t, $J_{H-H}$=8.6 Hz, 2H, $CH^{AP}$), 2.26 (br s, 2H, NH), 1.90-1.76 (m, 6H, $CH^{AP}$), 1.41 (d, $J_{H-H}$=8.0 Hz, 3H, $CH_3$) and 1.23 (d, $J_{H-H}$=8.0 Hz, 3H, $CH_3$). $^{13}$C NMR (125 MHz, DMSO-$d_6$, 298K): δ 172.3 (C=O), 167.8 (C=O), 70.6 (CH), 65.2 (CH), 60.6 ($C^{AP}$), 40.3, 33.3, 32.7, 22.1 ($C^{AP}$), 17.1 ($CH_3$) and 13.5 ($CH_3$).

Example 41: Reaction of 5-Amino-1-Pentanol Hydrochloride with Lactide in DMSO

A 25 ml round bottomed flask was loaded with 0.50 g of 5-amino-1-pentanol hydrochloride (1 equiv., 3.59 mmol), 1.036 g of lactide (2 equiv., 7.18 mmol) and 10 ml of dimethyl sulfoxide (DMSO). Reaction mixture was heated, vigorously stirred (8 hod/80° C.) and after that period filtered. All volatiles were evaporated under reduced pressure. The residue was dried to constant weight at 40° C./1 mbar.

The yield of product was 0.41 g (1.05 mmol, 29%). Anal. calcd for $C_{11}H_{21}NO_5$ (%): C (53.43), H (8.56), N (5.66), O (32.35); found: C (53.5), H (8.8). $^1$H NMR (500 MHz, DMSO-$d_6$, 298K): δ 4.93-4.87 (m, 2H, CH), 4.33-4.3 (m, 2H, CH), 3.63 (t, $J_{H-H}$=7.8 Hz, 2H, $CH^{AP}$), 3.01 (t, $J_{H-H}$=8.6 Hz, 2H, $CH^{AP}$), 2.72 (br s, 1H, NH), 1.92-1.89 (m, 6H, $CH^{AP}$), 1.44 (d, $J_{H-H}$=8.6 Hz, 6H, $CH_3$) and 1.26 (d, $J_{H-H}$=8.6 Hz, 6H, $CH_3$). $^{13}$C NMR (125 MHz, DMSO-$d_6$, 298K): δ 171.8 (C=O), 168.8 (C=O), 71.3 (CH), 66.3 (CH), 60.5 ($C^{AP}$), 40.8, 33.2, 32.8, 22.0 ($C^{AP}$), 19.3 ($CH_3$) and 15.1 ($CH_3$).

INDUSTRIAL APPLICABILITY

The present invention is useful in the preparation of environmentally friendly and biocompatible cosmetic and household products, especially for developing of new surfactants (emulsifiers), thickeners, builders, sequestering agents, hydrotropes etc., as well as for variation of existing raw materials.

The invention claimed is:

1. A process for preparing amides of lactyl lactate of general formula I

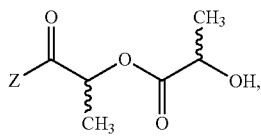

wherein Z is RR'N—, R is alkyl or aryl, and R' is alkyl, aryl, or H, from lactide, wherein the lactide reacts with an aliphatic or aromatic ammonium hydrohalide with 1 to 100 carbon atoms of general formula RR'NH·HX, where X is selected from Cl, Br and I in a non-chlorinated organic aliphatic or aromatic solvent or in a melted mixture of lactide under solvent free condition, and the reaction is carried out at a temperature in the range of 35 to 90° C. for 15 minutes to 8 hours.

* * * * *